(12) United States Patent
Nichols et al.

(10) Patent No.: US 7,500,479 B2
(45) Date of Patent: Mar. 10, 2009

(54) AEROSOL GENERATORS AND METHODS FOR PRODUCING AEROSOLS

(75) Inventors: Walter A. Nichols, Chesterfield, VA (US); Rajiv Gupta, Glen Allen, VA (US); Gene G. Faison, Richmond, VA (US); Kenneth A. Cox, Powhatan, VA (US)

(73) Assignee: Philip Morris USA Inc., Richmond, VA (US)

( * ) Notice: Subject to any disclaimer, the term of this patent is extended or adjusted under 35 U.S.C. 154(b) by 289 days.

(21) Appl. No.: 11/113,298

(22) Filed: Apr. 25, 2005

(65) Prior Publication Data

US 2005/0235991 A1   Oct. 27, 2005

Related U.S. Application Data

(60) Provisional application No. 60/564,591, filed on Apr. 23, 2004.

(51) Int. Cl.
*A61M 11/00* (2006.01)

(52) U.S. Cl. .............................. 128/200.23; 128/200.21

(58) Field of Classification Search ............ 128/200.14, 128/203.14–203.17, 203.26–203.27, 204.15, 128/204.17, 200.21, 200.22, 200.23
See application file for complete search history.

(56) References Cited

U.S. PATENT DOCUMENTS

| | | | |
|---|---|---|---|
| 1,276,245 A | 8/1918 | Millard et al. |
| 1,590,989 A | 6/1926 | Clayton |
| 1,867,526 A | 7/1932 | Anderson et al. |
| 2,470,990 A | 5/1949 | Kennedy |
| 2,962,843 A | 12/1960 | Hoelzer et al. |
| 2,991,500 A | 7/1961 | Hagen |
| 3,366,523 A | 1/1968 | Weber |
| 3,371,461 A | 3/1968 | Aronson |
| 3,382,644 A | 5/1968 | Vogt |
| 3,423,902 A | 1/1969 | Stroop |
| 3,453,797 A | 7/1969 | Soto |
| 3,575,757 A | 4/1971 | Smith |
| 3,660,189 A | 5/1972 | Troy |
| 3,669,359 A | 6/1972 | Focht |
| 3,817,017 A | 6/1974 | Titchenal |
| 3,857,485 A | 12/1974 | Frank |

(Continued)

FOREIGN PATENT DOCUMENTS

CN    1390984 A    1/2003

(Continued)

OTHER PUBLICATIONS

International Search Report and Opinion issued in PCT/US05/14095 on Nov. 30, 2006.

(Continued)

*Primary Examiner*—Justine R Yu
*Assistant Examiner*—Kristen C Matter
(74) *Attorney, Agent, or Firm*—Buchanan Ingersoll & Rooney PC

(57) ABSTRACT

An aerosol generator includes a flow passage having an inlet end, an outlet end, and a constriction in the flow passage at the outlet end. A heater is operable to heat liquid in the flow passage to produce a vapor, which is expelled from the outlet end of the flow passage.

52 Claims, 23 Drawing Sheets

U.S. PATENT DOCUMENTS

| | | |
|---|---|---|
| 3,971,192 A | 7/1976 | Soukup et al. |
| 3,974,042 A | 8/1976 | Angelini |
| 3,975,885 A | 8/1976 | Carlisle |
| 3,992,887 A | 11/1976 | Fisher |
| 4,005,063 A | 1/1977 | Gendrich et al. |
| 4,022,205 A | 5/1977 | Tenczar |
| 4,055,032 A | 10/1977 | Hammond |
| 4,056,940 A | 11/1977 | Fisher |
| 4,075,301 A | 2/1978 | Oswald |
| 4,135,180 A | 1/1979 | White |
| 4,159,803 A | 7/1979 | Cameto et al. |
| 4,169,344 A | 10/1979 | Ganz et al. |
| 4,187,846 A | 2/1980 | Lolachi et al. |
| 4,210,497 A | 7/1980 | Loqvist et al. |
| 4,240,999 A | 12/1980 | Decker, Jr. |
| 4,244,392 A | 1/1981 | Griswold et al. |
| 4,244,395 A | 1/1981 | Griswold et al. |
| 4,276,897 A | 7/1981 | Griswold |
| 4,333,495 A | 6/1982 | Griswold et al. |
| 4,364,408 A | 12/1982 | Griswold et al. |
| 4,376,500 A | 3/1983 | Banks et al. |
| 4,452,272 A | 6/1984 | Griswold |
| 4,484,577 A | 11/1984 | Sackner et al. |
| 4,510,734 A | 4/1985 | Banks et al. |
| 4,620,670 A | 11/1986 | Hughes |
| 4,704,844 A | 11/1987 | Mancini |
| 4,730,111 A | 3/1988 | Vestal et al. |
| 4,783,298 A | 11/1988 | Oda |
| 4,793,121 A | 12/1988 | Jamison |
| 4,839,117 A | 6/1989 | Swenson et al. |
| 4,862,676 A | 9/1989 | Mancini |
| 4,897,256 A | 1/1990 | Adjei et al. |
| 4,902,891 A | 2/1990 | Vestal |
| 5,230,366 A | 7/1993 | Marandi |
| 5,235,969 A | 8/1993 | Bellm |
| 5,275,424 A | 1/1994 | Watanabe |
| 5,301,710 A | 4/1994 | Marandi |
| 5,335,486 A | 8/1994 | Davis |
| 5,355,632 A | 10/1994 | Horie |
| 5,374,263 A | 12/1994 | Weiler |
| 5,406,974 A | 4/1995 | Griswold |
| 5,419,315 A | 5/1995 | Rubsamen |
| 5,433,243 A | 7/1995 | Griswold et al. |
| 5,446,025 A | 8/1995 | Lu et al. |
| 5,466,907 A | 11/1995 | Vuitton |
| 5,487,378 A | 1/1996 | Robertson et al. |
| 5,498,909 A * | 3/1996 | Hasunuma et al. .......... 257/754 |
| 5,500,067 A | 3/1996 | Jenkner |
| 5,527,445 A | 6/1996 | Palumbo et al. |
| 5,558,085 A | 9/1996 | Rubsamen et al. |
| 5,622,282 A | 4/1997 | Yazawa et al. |
| 5,635,068 A | 6/1997 | Marandi |
| 5,635,159 A | 6/1997 | Fu Lu et al. |
| 5,635,161 A | 6/1997 | Adjei et al. |
| 5,662,271 A | 9/1997 | Weston et al. |
| 5,676,931 A | 10/1997 | Adjei et al. |
| 5,698,496 A | 12/1997 | Fastnacht et al. |
| 5,700,366 A | 12/1997 | Steblianko et al. |
| 5,705,234 A | 1/1998 | Yamamoto et al. |
| 5,711,934 A | 1/1998 | Adjei et al. |
| 5,743,251 A | 4/1998 | Howell et al. |
| 5,816,902 A | 10/1998 | Watanabe et al. |
| 5,819,756 A | 10/1998 | Mielordt |
| 5,842,467 A | 12/1998 | Greco |
| 5,855,913 A | 1/1999 | Hanes et al. |
| 5,863,609 A | 1/1999 | Yamamoto |
| 5,888,477 A | 3/1999 | Gonda et al. |
| 5,937,890 A | 8/1999 | Marandi |
| 5,960,792 A | 10/1999 | Lloyd et al. |
| 5,985,309 A | 11/1999 | Edwards et al. |
| 5,997,956 A | 12/1999 | Hunt et al. |
| 6,007,591 A | 12/1999 | Watanabe |
| 6,009,869 A | 1/2000 | Corbeil |
| 6,126,515 A | 10/2000 | Horie et al. |
| 6,132,653 A | 10/2000 | Hunt et al. |
| 6,146,714 A | 11/2000 | Beyer et al. |
| 6,155,268 A | 12/2000 | Takeuchi |
| 6,158,428 A | 12/2000 | Mecikalski |
| 6,207,522 B1 | 3/2001 | Hunt et al. |
| 6,212,078 B1 | 4/2001 | Hunt et al. |
| 6,230,943 B1 | 5/2001 | Miyamoto et al. |
| 6,234,167 B1 | 5/2001 | Cox et al. |
| 6,270,835 B1 | 8/2001 | Hunt et al. |
| 6,276,347 B1 | 8/2001 | Hunt |
| 6,287,449 B1 | 9/2001 | Horie et al. |
| 6,315,638 B1 | 11/2001 | Marukawa |
| 6,329,899 B1 | 12/2001 | Hunt et al. |
| 6,368,665 B1 | 4/2002 | Hunt et al. |
| 6,372,364 B1 | 4/2002 | Hunt et al. |
| 6,390,076 B2 | 5/2002 | Hunt |
| 6,390,090 B1 | 5/2002 | Piper |
| 6,396,387 B1 | 5/2002 | Hunt et al. |
| 6,403,245 B1 | 6/2002 | Hunt |
| 6,416,870 B1 | 7/2002 | Hunt et al. |
| 6,433,993 B1 | 8/2002 | Hunt et al. |
| 6,439,430 B1 | 8/2002 | Gilroy, Sr. et al. |
| 6,491,233 B2 | 12/2002 | Nichols |
| 6,494,202 B2 | 12/2002 | Farmer |
| 6,501,052 B2 | 12/2002 | Cox et al. |
| 6,508,810 B1 | 1/2003 | Ouchi et al. |
| 6,585,134 B2 | 7/2003 | Farris |
| 6,601,776 B1 | 8/2003 | Oljaca et al. |
| 6,624,382 B2 | 9/2003 | Kling |
| 6,640,050 B2 | 10/2003 | Nichols et al. |
| 6,701,921 B2 | 3/2004 | Sprinkel, Jr. et al. |
| 6,726,416 B2 | 4/2004 | Shoup |
| 6,729,334 B1 | 5/2004 | Baran |
| 2001/0012600 A1 | 8/2001 | Hunt et al. |
| 2001/0020469 A1 | 9/2001 | Hunt |
| 2001/0039919 A1 | 11/2001 | Hunt et al. |
| 2001/0042719 A1 | 11/2001 | Levy |
| 2002/0010892 A1 | 1/2002 | Lodge et al. |
| 2002/0015797 A1 | 2/2002 | Hunt et al. |
| 2002/0058143 A1 | 5/2002 | Hunt et al. |
| 2002/0068082 A1 | 6/2002 | Fuisz |
| 2002/0069826 A1 | 6/2002 | Hunt et al. |
| 2002/0145845 A1 | 10/2002 | Hunt et al. |
| 2002/0176989 A1 | 11/2002 | Knudsen et al. |
| 2003/0013235 A1 | 1/2003 | Featherby et al. |
| 2003/0016117 A1 | 1/2003 | Senk et al. |
| 2003/0021885 A1 | 1/2003 | Shoup et al. |
| 2003/0047617 A1 | 3/2003 | Shanmugham et al. |
| 2003/0056791 A1* | 3/2003 | Nichols et al. ......... 128/203.16 |
| 2003/0089384 A1 | 5/2003 | Sato et al. |
| 2003/0098102 A1 | 5/2003 | Perry et al. |
| 2003/0098103 A1 | 5/2003 | Perry et al. |
| 2003/0106551 A1 | 6/2003 | Sprinkel, Jr. et al. |
| 2003/0136404 A1 | 7/2003 | Hindle et al. |
| 2003/0145258 A1 | 7/2003 | Warner et al. |
| 2003/0215644 A1 | 11/2003 | Deshpande et al. |
| 2003/0218054 A1 | 11/2003 | Koenigsmann et al. |
| 2003/0228500 A1 | 12/2003 | Schmitt et al. |
| 2003/0230303 A1 | 12/2003 | Nichols et al. |
| 2004/0009174 A1 | 1/2004 | Arndt et al. |
| 2004/0009388 A1 | 1/2004 | Faguy |
| 2004/0025865 A1 | 2/2004 | Nichols et al. |
| 2004/0031546 A1 | 2/2004 | Perry et al. |
| 2004/0038024 A1 | 2/2004 | Yamaguchi et al. |
| 2004/0041245 A1 | 3/2004 | Quinlan et al. |
| 2004/0048433 A1 | 3/2004 | Takahashi |
| 2004/0050383 A1 | 3/2004 | Cox et al. |
| 2004/0052461 A1 | 3/2004 | Hunt et al. |
| 2004/0066250 A1 | 4/2004 | Hunt et al. |
| 2004/0072504 A1 | 4/2004 | Tada |

| | | | |
|---|---|---|---|
| 2004/0079360 | A1 | 4/2004 | Coffee et al. |
| 2004/0083568 | A1 | 5/2004 | Morioka et al. |
| 2004/0096643 | A1 | 5/2004 | Sato et al. |
| 2004/0124259 | A1 | 7/2004 | Guezennec et al. |
| 2004/0163646 | A1* | 8/2004 | Schuster et al. ........ 128/203.26 |
| 2004/0195364 | A1 | 10/2004 | Piper |
| 2005/0150489 | A1* | 7/2005 | Dunfield et al. ........ 128/200.14 |

FOREIGN PATENT DOCUMENTS

| | | |
|---|---|---|
| CN | 1401823 A | 3/2003 |
| GB | 2178342 A | 7/1986 |
| WO | WO 02/16059 | 2/2002 |

OTHER PUBLICATIONS

Bank et al., "Flow Injection Spray Sample Deposition for Electrothermal Atomization Atomic Absorption Spectroscopy": *Spectrochimica Acta*, 43B, 983-987 (1988).

Clifford et al., "Particle Size Measurements in the Submicron Range by the Differential Electromobility Technique: Comparison of Aerosols from Thermospray, Ultrasonic Pneumatic and Frit-Type Nebulizers", *Spectrochimica Acta*, 48B: 1221-1235 (1993).

Design Guide, "Dynamic Balancing of Hydronic Systems", Griswold Controls (2003).

"Diabetes Epidemic Triggers Boom in Drug Candidates", *Health News, Today's Health News, Reuters Health*, available at http://www.wellspan.org/HealthNews/reuters/NewsStory0617200326.htm?DisplayPrinthead, Jun. 17, 2003—accessed Nov. 26, 2003.

Griswold Controls, *IR-IS Fluctuated Isolator*, available at http://GriswoldControls.com (last visited Sep. 19, 2006).

Griswold Controls, *Automatic Flux Control Cartidge*, available at http://GriswoldControls.com (last visited Sep. 19, 2006).

Griswold Controls, *Uni-Flange*, available at http://GriswoldControls.com (last visited Sep. 19, 2006).

Horne et al., "Eli Lilly Wins Court Fight Over Inhalable Insulin, But Questions Remain", *KRTBN Knight-Ridder Tribune Business News* (*Indianapolis Start and News*—Indiana), (2002).

Koropchak et al., "Effects of Capillary Diameter on Thermospray Sample Introduction to Inductively Coupled Plasma Atomic Emission Spectroscopy", *Journal of Analytical Atomic Spectroscopy*, 3:799-802 (1988).

Koropchak et al., "Thermospray Sample Introduction to Atomic Spectrometry", *Critical Reviews in Analytical Chemistry*, 23(3):113-141 (1992).

Koropchak et al., "Fused Silica Aperture Thermospray Sample Introduction to Inductively Coupled Plasma Atomic Emission Spectroscopy", *Spectrochimica Acta*, 47B(6):825-834 (1992).

Mendosa, Rick, "Inhaled Insulin", www.Mendosa.com—*Your Online Diabetes Resource*, available at http://www.mendosa.com/inhaled.htm, Sep. 15, 2000—accessed Nov. 26, 2003.

Mendosa, Rick, "Waiting to Inhale", www.Mendosa.com—*Your Online Diabetes Resource*, available at http://www.mendosa.com/inhaled_insulin.htm, Apr. 27, 2000—accessed Nov. 26, 2003.

Mora et al., "Behavior of the Thermospray Nebulizer as a System for the Introduction of Organic Solutions in Flame Atomic Absorption Spectrometry", *Spectrochimica Acta*, 51B:1535-1549 (1996).

Morrissey, Brian, "Don't Write Off Insulin Yet: Pulmonary Delivery Promises to Breath New Life into this $3 Billion Market", *The Frankel Group*, Jun. 28, 2000.

"Respimat Soft Mist Inhaler Is Easy to Use (product literature)", www.Respimat.com, by Boehringer Ingelheim (2003).

Seltzer, Jed, "Update 3-Nektar Inhaled Insulin Product Proves Safe" *Reuters*, (2003).

Vestal and Fergusson, "Thermospray Liquid Chromatograph/Mass Spectrometer Interface with Direct Electrical Heating of the Capillary", *Analytical Chemistry*, 57:2373-2378 (1985).

* cited by examiner

AEROSOL GENERATORS AND METHODS FOR PRODUCING AEROSOLS

RELATED APPLICATIONS

The present application claims the benefit of U.S. Provisional Application Ser. No. 60/564,591 filed on Apr. 23, 2004, which is hereby incorporated by reference.

FIELD OF THE INVENTION

The present invention relates generally to aerosol generators and methods for producing aerosols.

BACKGROUND

Aerosols can be used in a wide variety of applications. For example, it is known to use aerosols for medical applications including the treatment of respiratory ailments, such as by delivering drugs via aerosol sprays including finely divided particles of liquids and/or solids, for example, powders, medicaments, etc., which are inhaled into a patient's lungs. Aerosols can also be used in other applications, such as introducing scents into rooms, distributing insecticides, injecting fuels into engines of vehicles, and delivering paints, lubricants and other substances.

Aerosol generators and methods of producing aerosols with the aerosol generators are disclosed, for example, in commonly-owned U.S. Pat. Nos. 5,743,251, 6,234,167 and 6,491,233, each of which is hereby incorporated by reference in its entirety.

For many applications, the effectiveness of aerosol generators can, at least in part, be related to the particle size distribution of the aerosols that they produce. Aerosol particle size distribution can affect where aerosol particles are deposited, as well as how well the particles are utilized once they are deposited. For example, in the treatment of medical ailments, it may be desirable to deposit a fluid formulation within a patient's lungs using an aerosol. In such cases, the aerosol particle size distribution can affect whether significant quantities of the formulation are deposited in the patient's throat or mouth instead of in the patient's lungs where the formulation would be more effective. Additionally, less favorable particle size distributions may take longer for the formulation to be absorbed once deposited.

In some applications, aerosol generators may be designed to deliver formulations that can, for example, be made up of excipients such as water, ethanol and mixtures of both that are combined with various medicaments. Some aerosol generators operate by passing the formulations through a tube to produce an aerosol. Clogging in such formulation delivery tubes can affect the aerosol generators' ability to accurately and repeatedly meter out appropriate quantities of the formulations, to generate an aerosol having a desired particle size distribution and can otherwise hamper the effectiveness of the generator. Thus, a need exists in the art to address deficiencies in known aerosol generators.

SUMMARY

The present invention provides improved aerosol generators as well as improved methods for making and using aerosol generators. One embodiment of the aerosol generator comprises a flow passage including an inlet end, an outlet end, a first flow section, and a constriction at the outlet end, which defines a second flow section of the flow passage downstream from the first flow section. A heater is arranged along the flow passage and is operable to heat fluid in the first flow section to produce vapor. The heated fluid is expelled from the outlet end to form an aerosol.

Another embodiment of the aerosol generator is a handheld device, which comprises a flow passage including an inlet end, an outlet end, a first flow section, and a constriction at the outlet end, which defines a second flow section of the flow passage downstream from the first flow section. A heater is arranged along the flow passage and adapted to heat liquid in the first flow section to produce vapor. The heated fluid is expelled from the outlet end. A mouthpiece through which a user can draw aerosol from the aerosol generator is arranged in fluid communication with the outlet end of the flow passage so as to form an aerosol.

Yet another embodiment of the aerosol generator comprises a flow passage including an inlet end, an outlet end, a first flow section, and a constriction at the outlet end of the flow passage, which defines a second flow section of the flow passage downstream from the first flow section. A liquid source is in flow communication with the inlet end of the flow passage, and contains a liquid formulation including a medicament. A heater is arranged along the flow passage and is adapted to heat the liquid formulation in the first flow section to produce vapor. This fluid is expelled from the outlet end so as to form an aerosol.

A further embodiment of the aerosol generator comprises a flow passage including an inlet end, an outlet end, a first flow section, and a constriction at the outlet end, which defines a second flow section of the flow passage downstream from the first flow section. The aerosol generator includes a power supply adapted to supply power to a heater arranged along the flow passage, and a controller adapted to control operation of the power supply to supply an effective amount of power to the heater to heat liquid in the first flow section to produce a desired quantity of vapor. The vapor and any entrained liquid is expelled from the outlet end so as to form an aerosol.

In another embodiment, the aerosol generator comprises a flow passage including an inlet end, an outlet end, a first flow section, and a constriction at the outlet end, which defines a second flow section of the flow passage downstream from the first flow section. A heater is arranged along the flow passage and is operable to heat liquid in the first flow section to produce vapor which is expelled together with any entrained liquid from the outlet end so as to form an aerosol. The aerosol generator includes a first electrode attached to the heater and a second electrode attached to the heater downstream of the first electrode. The second electrode is of a material having a smaller resistance than a material of the heater.

Any of these embodiments may optionally further include a device for cooling the heated fluid, or vapor together with any entrained liquids, as it flows near the outlet end of the flow passage.

The constriction can have various forms, such as an insert in the flow passage, or a formed end of the flow passage. The flow passage can be of various materials and can have monolithic or multi-piece constructions.

The aerosol generator can produce aerosols from liquid formulations including a carrier and various medicaments. For example, the carrier can be a volatile carrier, such as water, ethanol or mixtures thereof, or a non-volatile carrier. Various medicaments can be used including, for example, analgesics, anginal preparations, anti-allergics, antibiotics, antihistamines, antitussives, bronchodilators, diuretics, anticholinergics, hormones and anti-flammatory agents.

An embodiment of a method of producing an aerosol, comprises supplying a liquid to the inlet end of a flow passage including an outlet end, a first flow section, and a constriction at the outlet end which defines a second flow section of the flow passage downstream from the first flow section; and heating the liquid in the first flow section to produce vapor which is expelled from the outlet end into ambient air so as to form an aerosol.

In an alternative embodiment of the above method, the fluid passes through a third flow section of the flow passage where the fluid is cooled as it passes through and is expelled.

DRAWINGS

Figure 18:
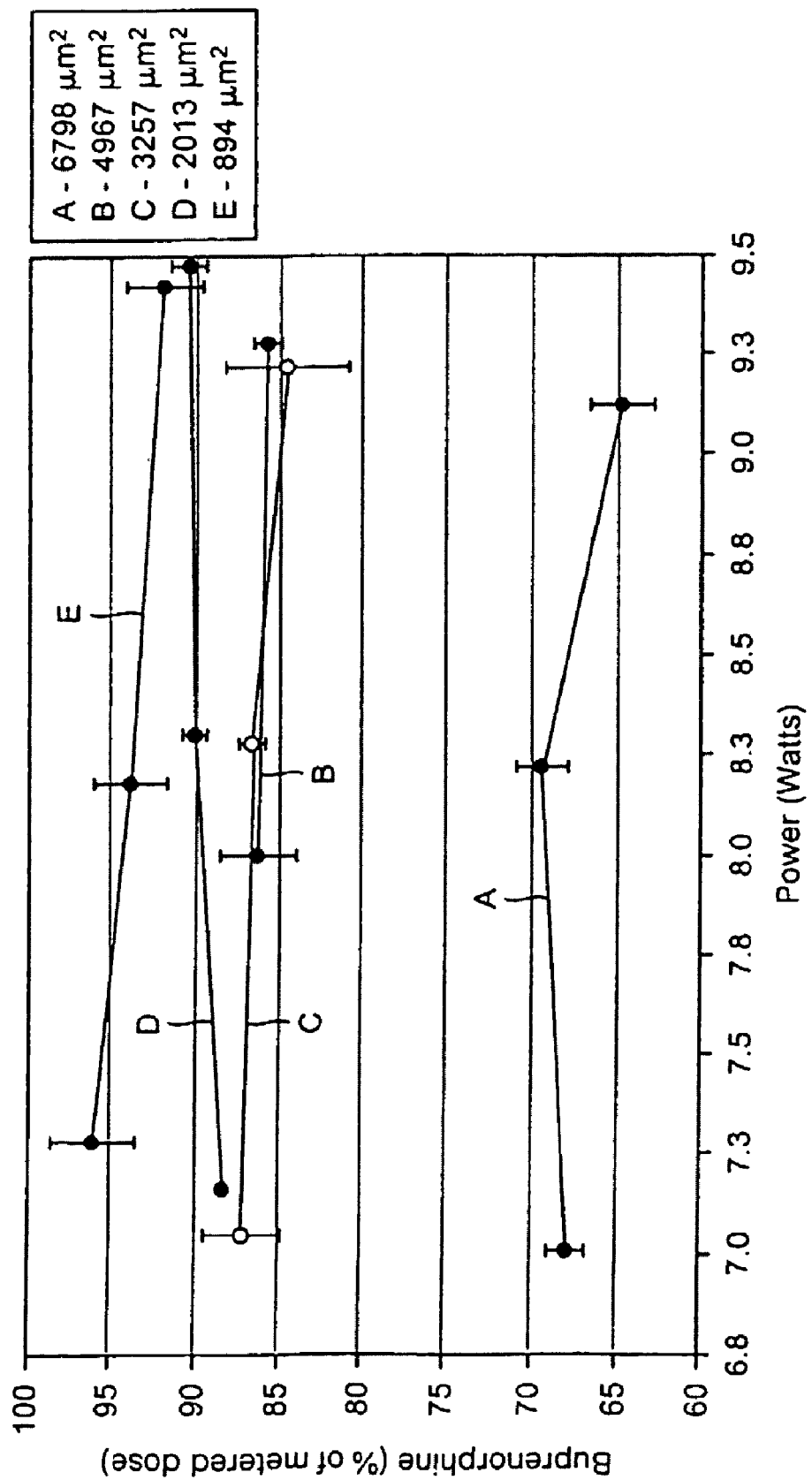

FIG. 18 shows the relationship between % recovery of buprenorphine HCl aerosol particles and power applied to the heater of an aerosol generator including a flow passage having a constriction in the form of a formed tip for an aerosol produced from a liquid formulation containing 1.5% buprenorphine HCl in an 95% ethanol/5% water for formed tips having different open cross-sectional areas of 894 $\mu m^2$, 2013 $\mu m^2$, 3257 $\mu m^2$, 4967 $\mu m^2$ and 6798 $\mu m^2$.

Figure 19:
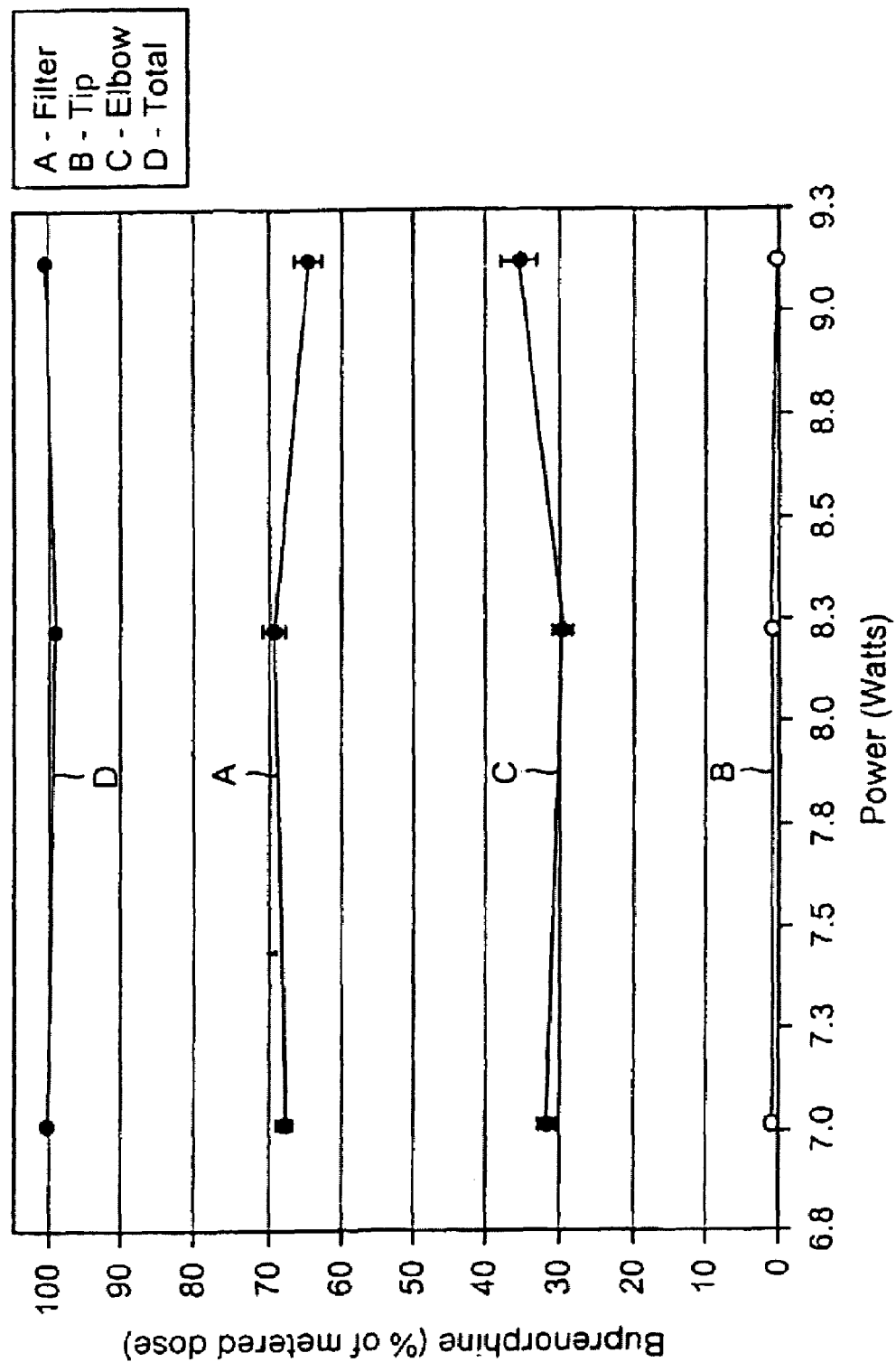
Figure 20:
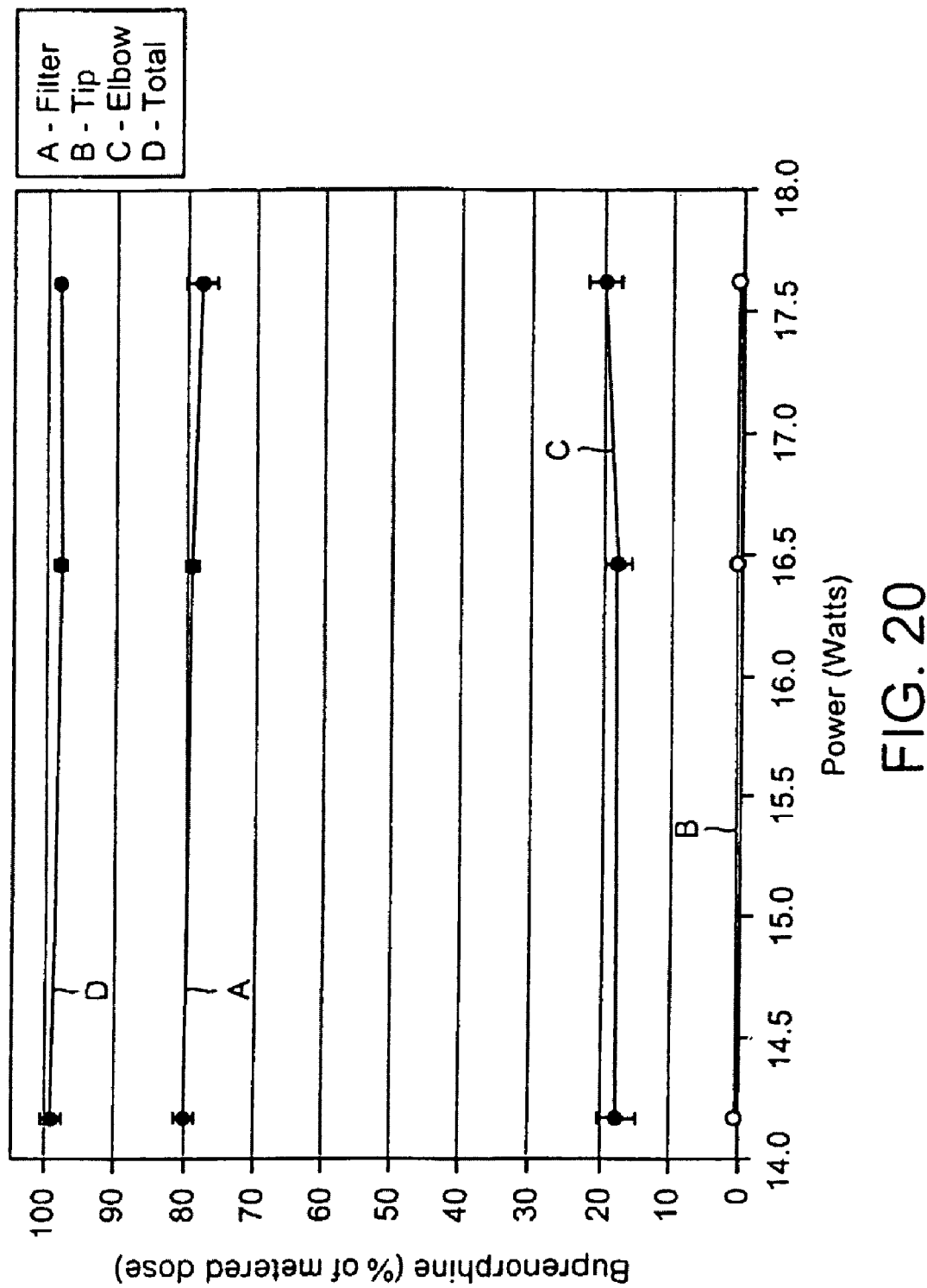

FIG. 19 shows the relationship between % recovery of buprenorphine HCl aerosol particles and power applied to the heater of an aerosol generator including a flow passage having a formed tip constriction with an open cross-sectional area of 6798 $\mu m^2$ for an aerosol produced from a liquid formulation containing 1.5% buprenorphine HCl in an 95% ethanol/5% water for a liquid flow rate of 10 $\mu L/sec$ FIG. 20 shows the relationship between % recovery of buprenorphine HCl aerosol particles and power applied to the heater of an aerosol generator including a flow passage having a formed tip constriction with an open cross-sectional area of 6798 $\mu m2$ for an aerosol produced from a liquid formulation containing 1.5% buprenorphine HCl in an 95% ethanol/5% water for a liquid flow rate of 20 $\mu L/sec$.

Figure 21:
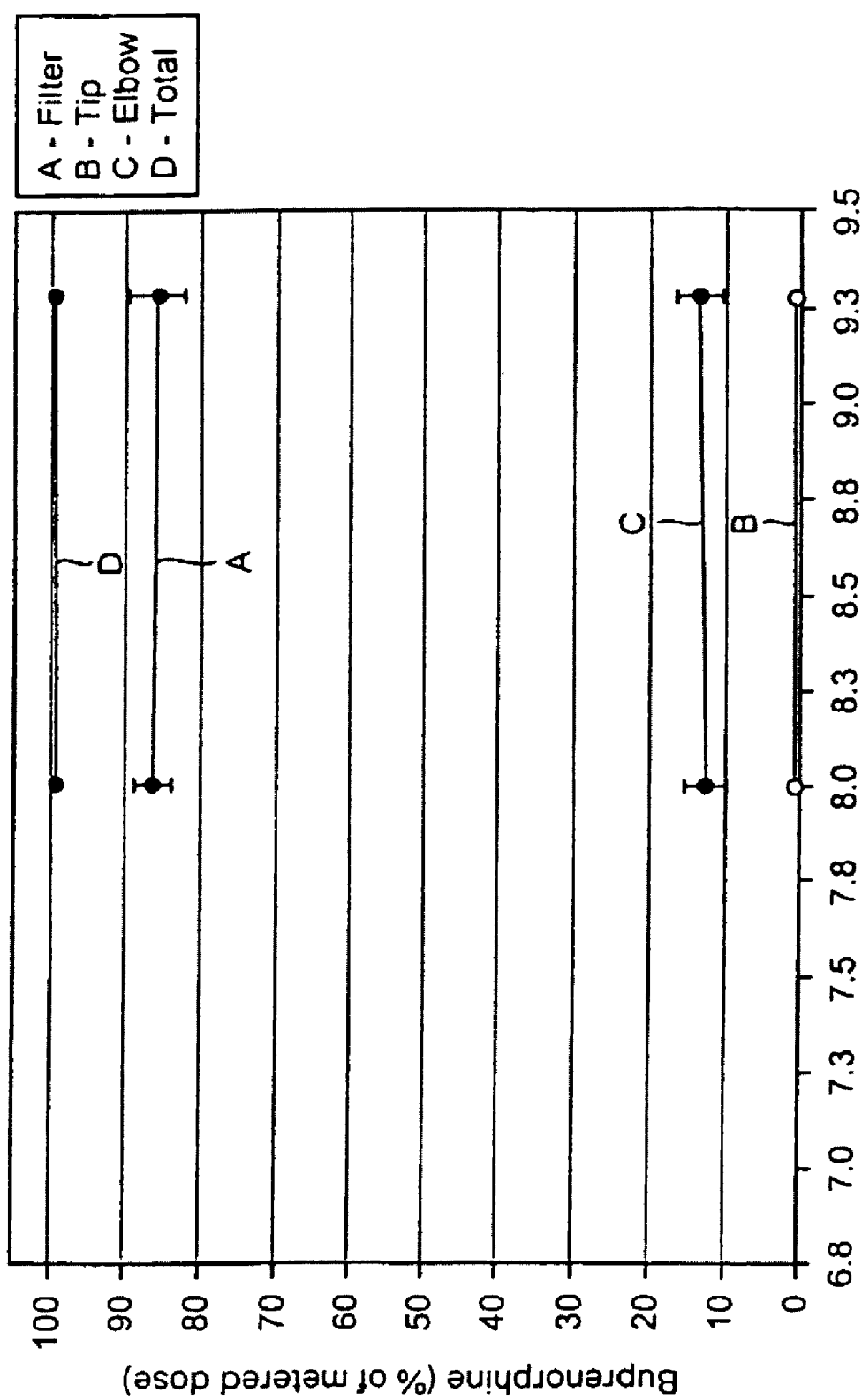

FIG. 21 shows the relationship between % recovery of buprenorphine HCl aerosol particles and power applied to the heater of an aerosol generator including a flow passage having a formed tip constriction with an open cross-sectional area of 4968 $\mu m^2$ for an aerosol produced from a liquid formulation containing 1.5% buprenorphine HCL in an 95% ethanol/5% water for a liquid flow rate of 10 $\mu L/sec$.

Figure 22:
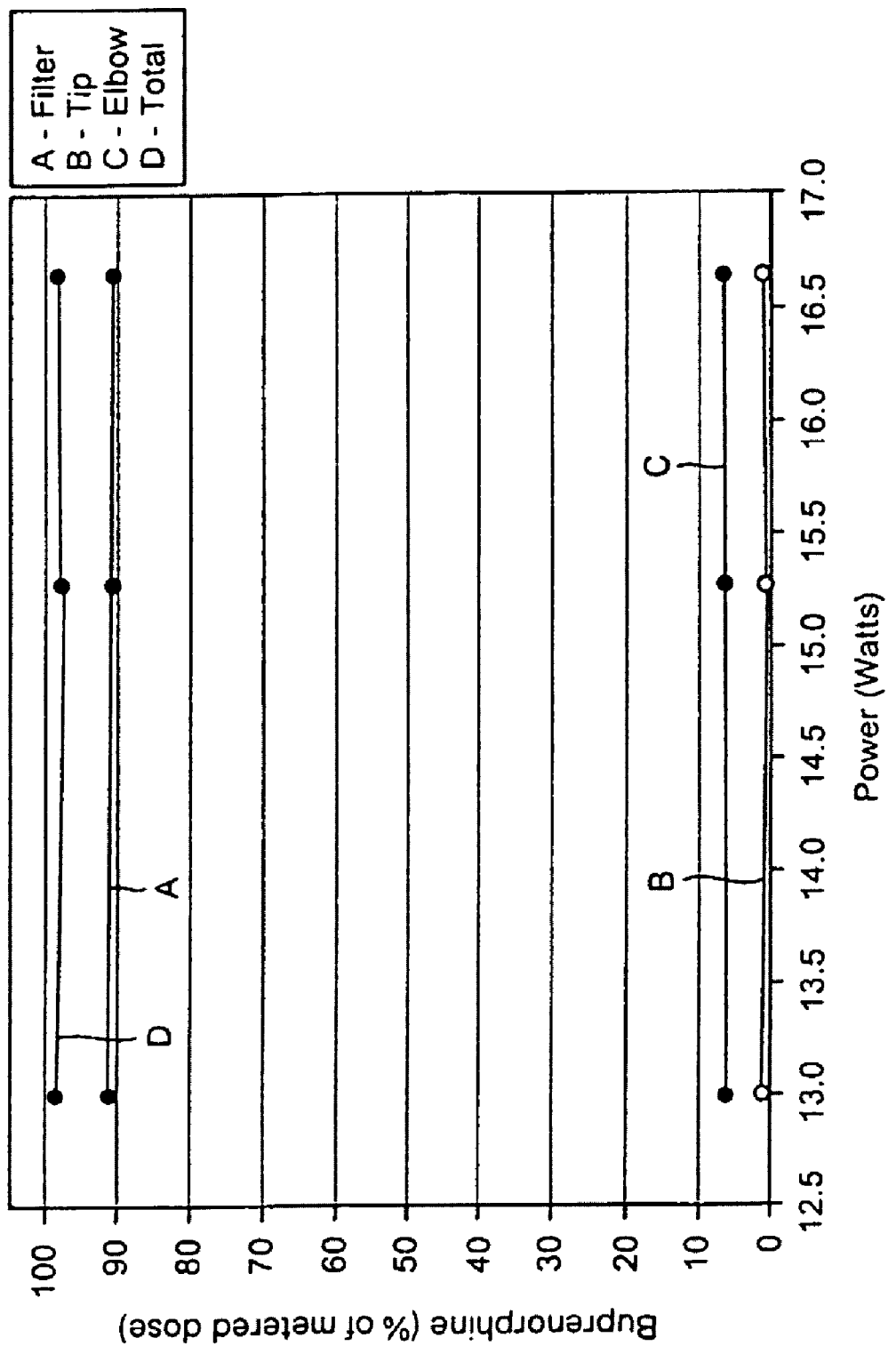
Figure 23:
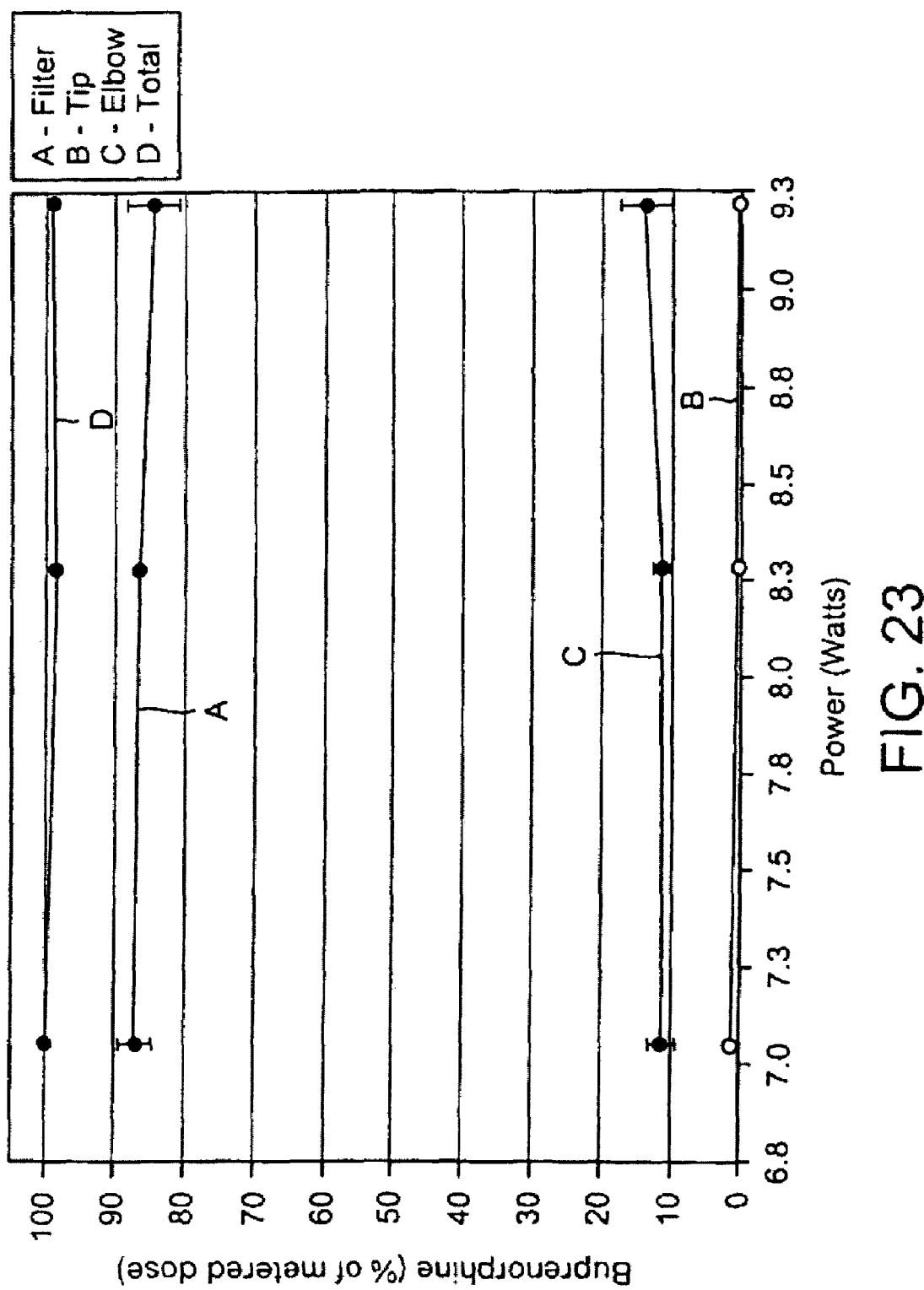

FIG. 22 shows the relationship between % recovery of buprenorphine HCl aerosol particles and power applied to the heater of an aerosol generator including a flow passage having a formed tip constriction with an open cross-sectional area of 4968 $\mu m^2$ for an aerosol produced from a liquid formulation containing 1.5% buprenorphine HCl in an 95% ethanol/5% water for a liquid flow rate of 20 $\mu L/sec$ FIG. 23 shows the relationship between % recovery of buprenorphine HCl aerosol particles and power applied to the heater of an aerosol generator including a flow passage having a formed tip constriction with an open cross-sectional area of 3257 $\mu m^2$ for an aerosol produced from a liquid formulation containing 1.5% buprenorphine HCL in an 95% ethanol/5% water for a liquid flow rate of 10 $\mu L/sec$.

Figure 24:
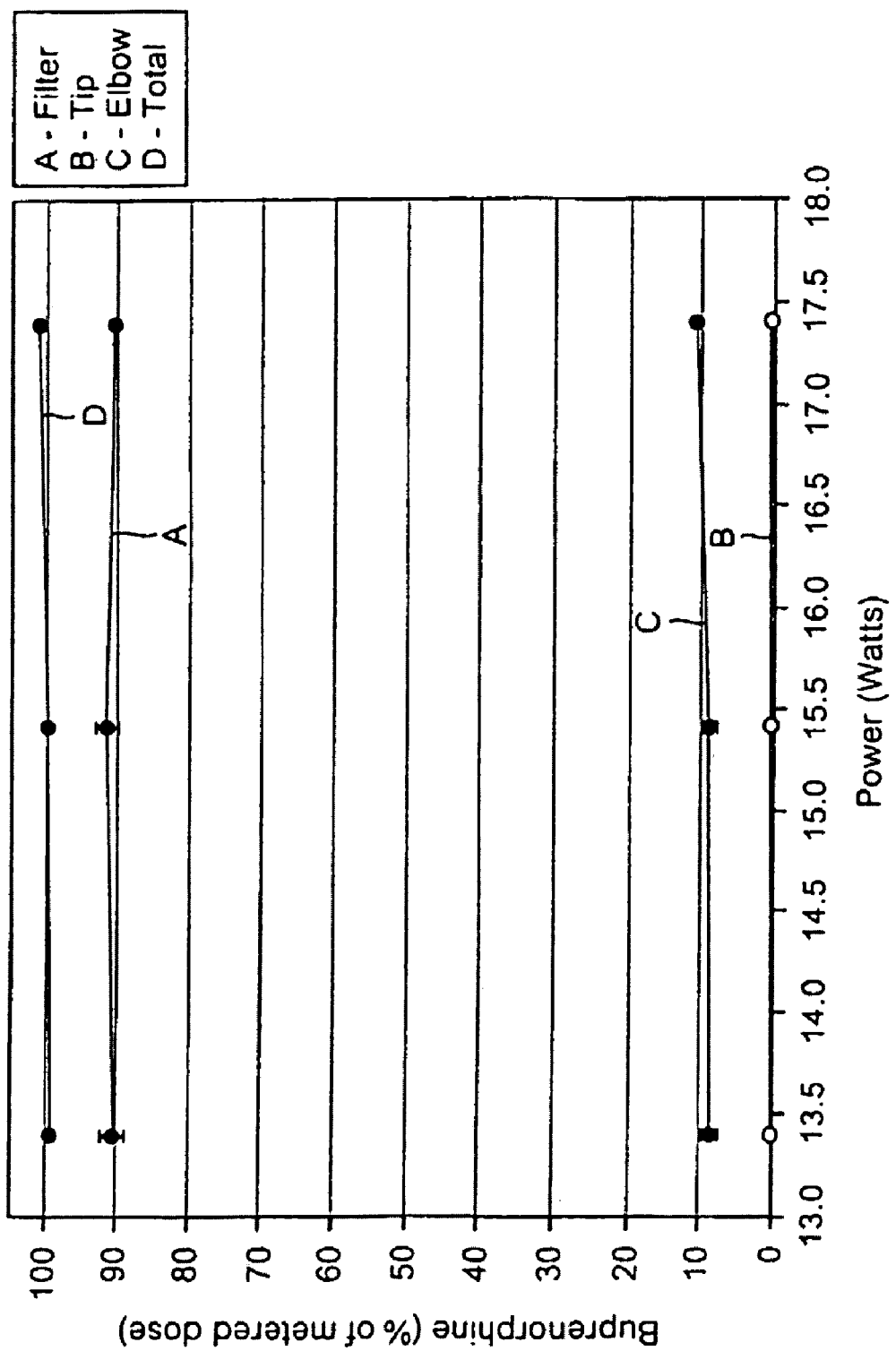

FIG. 24 shows the relationship between % recovery of buprenorphine HCl aerosol particles and power applied to the heater of an aerosol generator including a flow passage having a formed tip constriction with an open cross-sectional area of 3257 $\mu m^2$ for an aerosol produced from a liquid formulation containing 1.5% buprenorphine HCl in an 95% ethanol/5% water for a liquid flow rate of 20 $\mu L/sec$.

Figure 25:
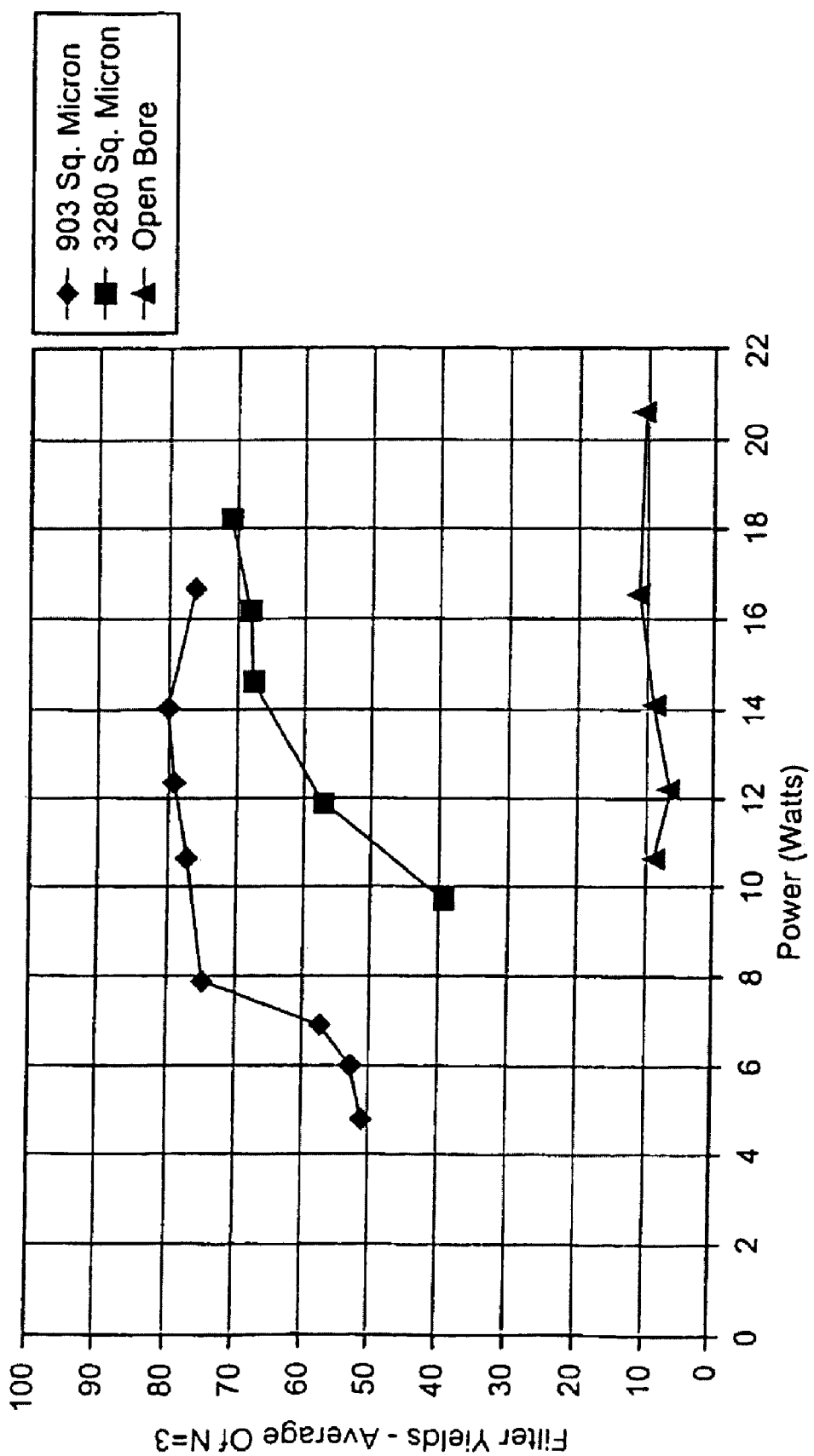

FIG. 25 shows the relationship between % recovery of cromolyn sodium aerosol particles and power applied to the heater of an aerosol generator including a flow passage without a constriction, a flow passage having a formed tip constriction with an open cross-sectional area of 903 µm² and a flow passage having a formed tip with an open cross-sectional area of 3280 µm² for aerosol produced from a liquid formulation containing 3% cromolyn sodium in 100% water.

Figure 26:
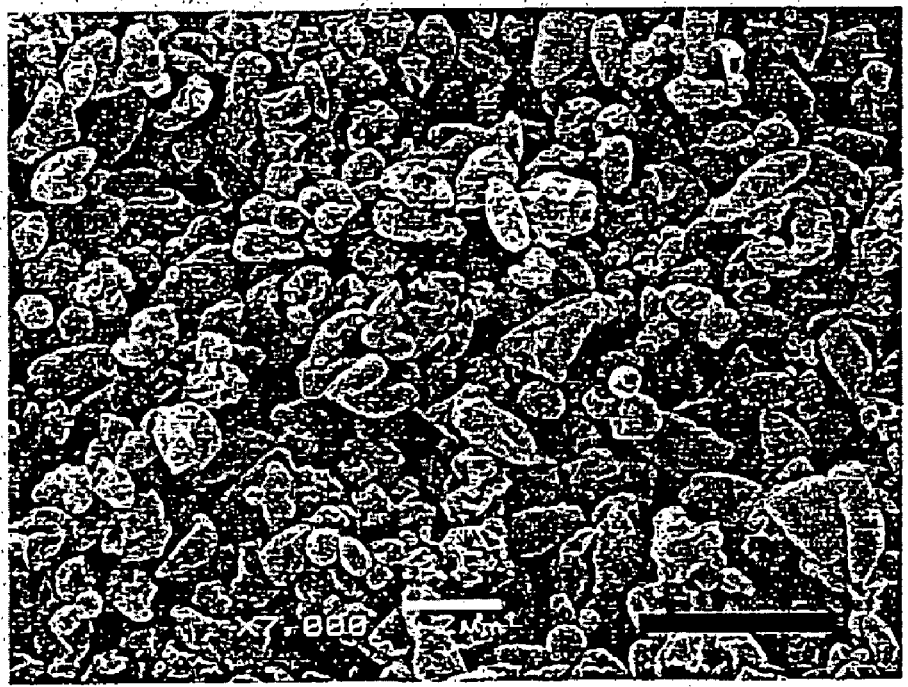

FIG. 26 is a scanning electron microscope (SEM) micrograph (7,000×) of aerosolized insulin particles produced from a HUMULIN R formulation.

Figure 27:
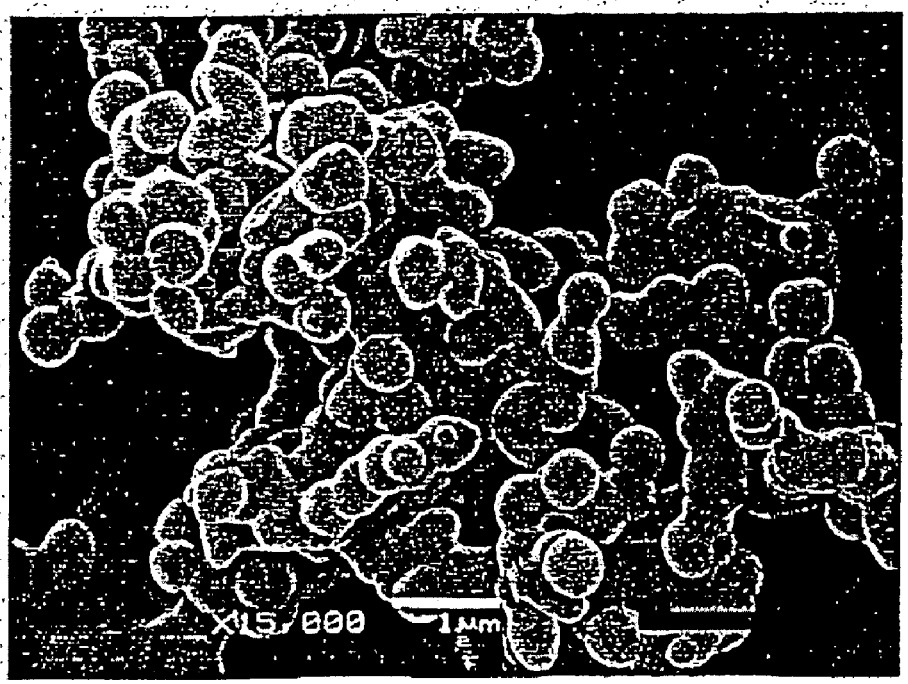
Figure 28:
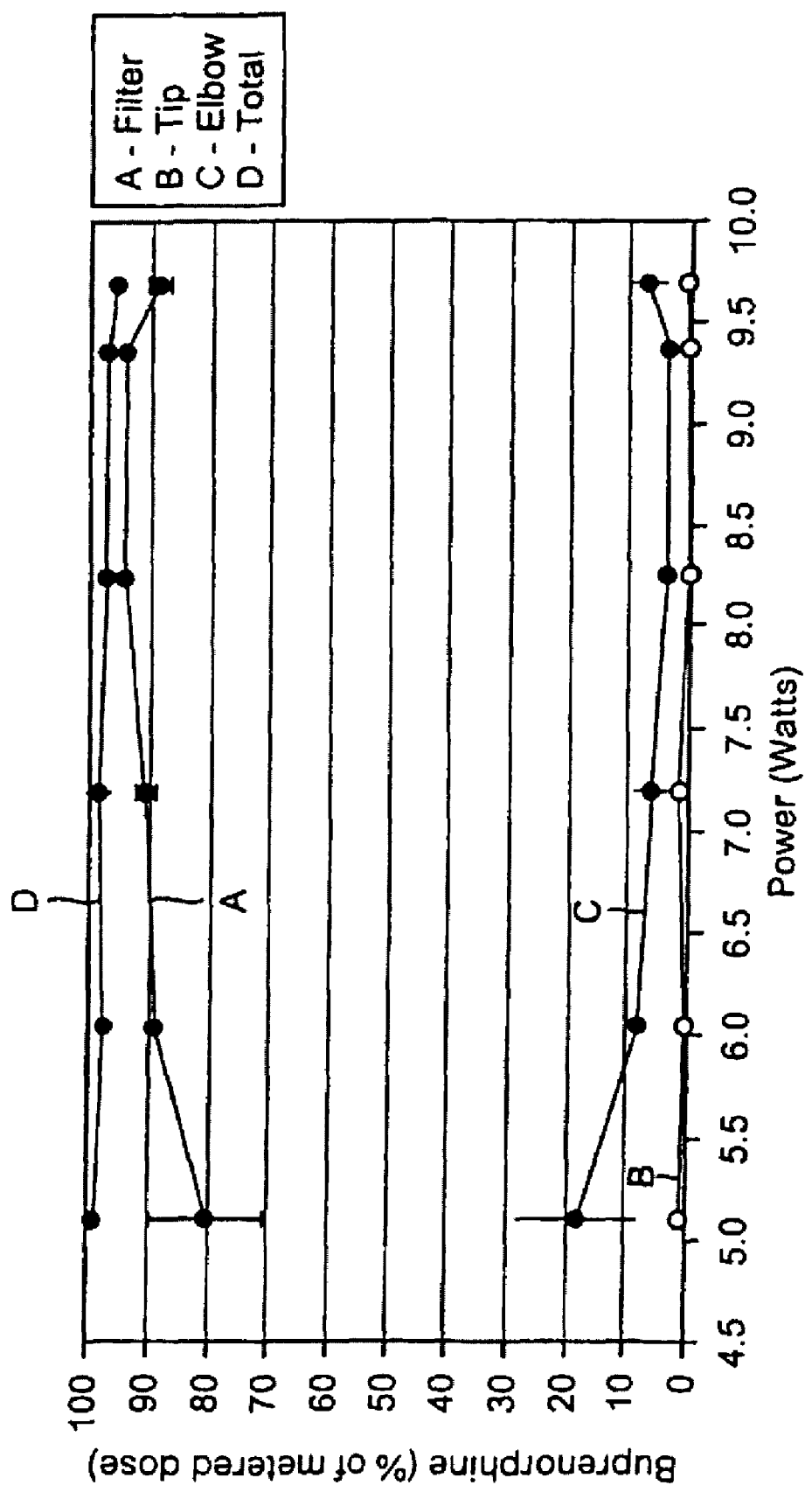

FIG. 27 is an SEM micrograph (15,000×) of aerosolized insulin particles produced from a HUMULIN R formulation FIG. 28 shows the relationship between % recovery of buprenorphine HCl aerosol particles and power applied to the heater of an aerosol generator including a flow passage having a length of 25 mm with a formed tip for an aerosol produced from a liquid formulation containing 1.5% buprenorphine HCl in 95% ethanol/5% water.

Figure 29:
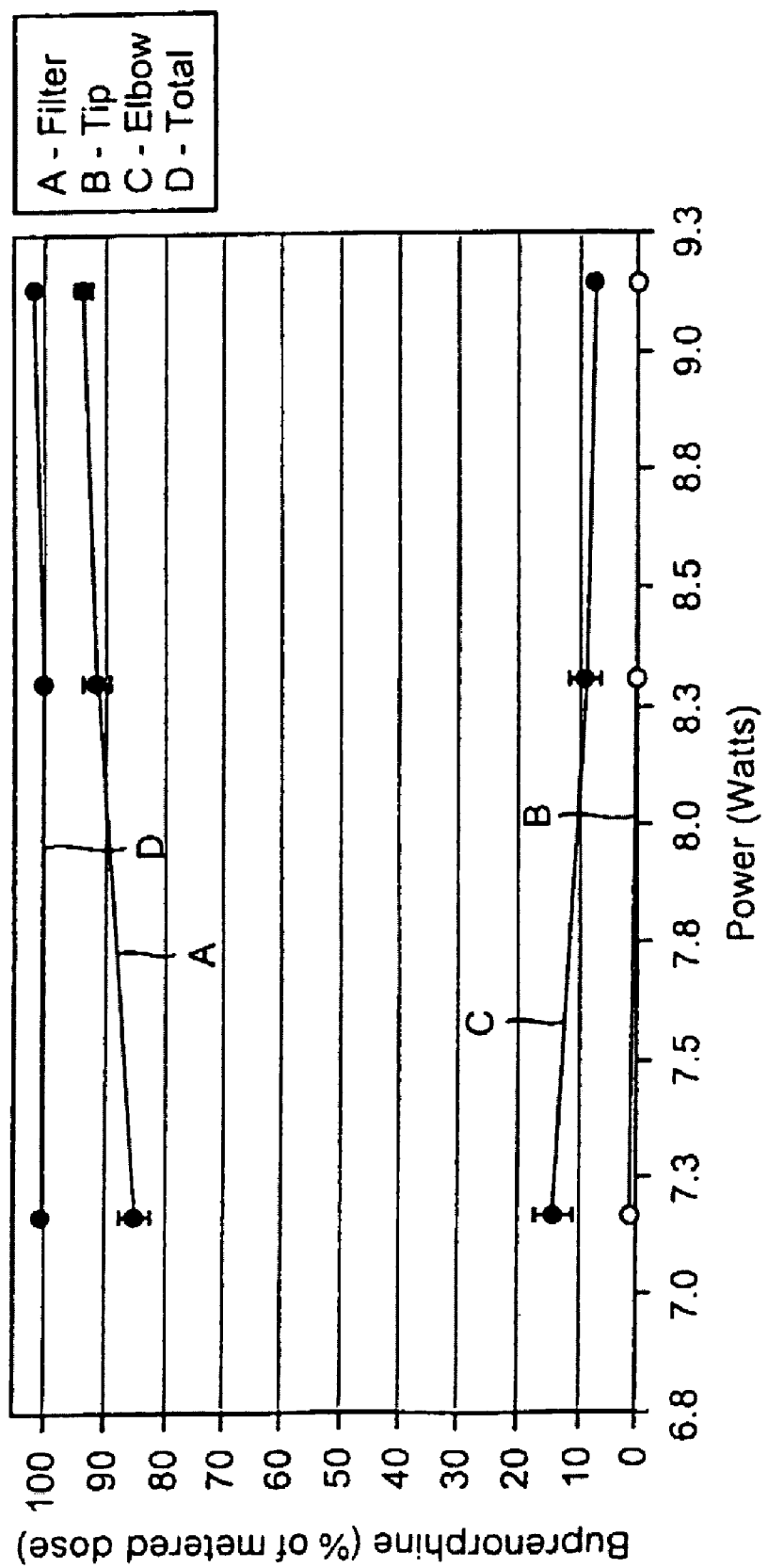

FIG. 29 shows the relationship between % recovery of buprenorphine HCl aerosol particles and power applied to the heater of an aerosol generator including a flow passage having a length of 35 mm with a formed tip for an aerosol produced from a liquid formulation containing 1.5% buprenorphine HCl in 95% ethanol/5% water.

Figure 30:
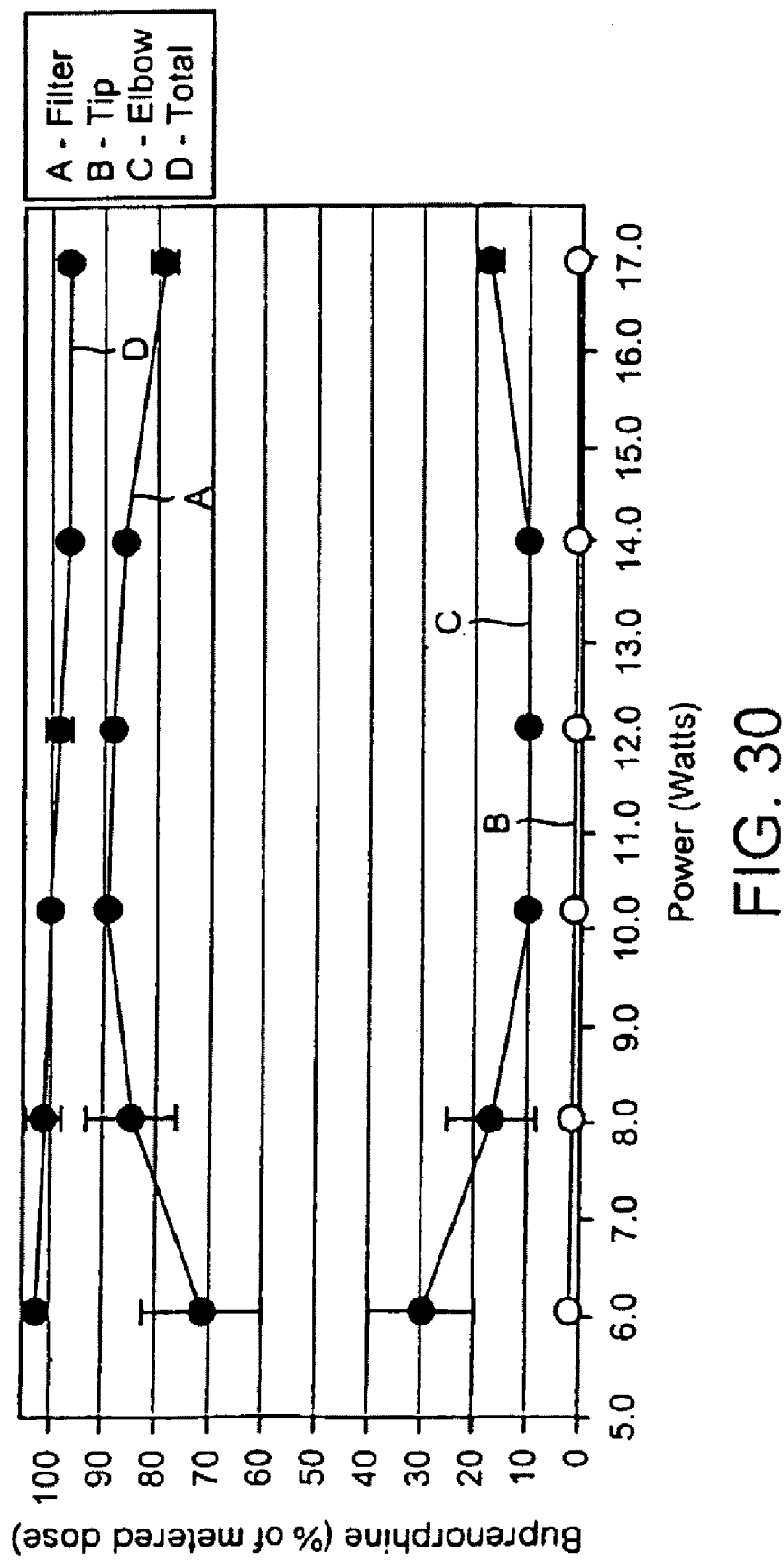

FIG. 30 shows the relationship between % recovery of buprenorphine HCl aerosol particles and power applied to the heater of an aerosol generator including a flow passage having a length of 25 mm with a formed tip for an aerosol produced from a liquid formulation containing 1.5% buprenorphine HCl in 95% ethanol/5% water at a flow rate of 20 µL/sec.

DETAILED DESCRIPTION

Aerosol generators that are useful for producing aerosols from liquids are provided. The aerosol generators include a flow passage into which a liquid is introduced. Aerosols can be produced by heating the liquid in the flow passage to transform a portion of the liquid to a vapor, and expelling the fluid from the flow passage. The expelled fluid can be mixed with air to produce an aerosol.

Preferred embodiments of the aerosol generators can be operated to produce aerosols from liquids that contain a highly-volatile liquid and a second component, which is aerosolized. For example, the highly-volatile liquid can be a highly-volatile liquid excipient for delivering a medicament. Advantageously, the excipient is readily volatilized with a minimum energy input. By way of non-limiting example highly-volatile liquids can include water, as well as other liquids having a boiling point similar to that of water. Another preferred high-volatility carrier is ethyl alcohol (ethanol), which has a boiling point of about 78° C. at a pressure of 1 atmosphere. Ethanol is a Federal Drug Administration (FDA) accepted excipient in drug products administered via inhalation. Ethanol can be used in combination with other liquids, for example, in ethanol/water solutions. In an exemplary embodiment, the excipient can comprise about 20% to 80% by volume of water and about 80% to 20% by volume ethanol. In another exemplary embodiment, the excipient can comprise about 80% to 100% by volume water and up to about 20% by volume of ethanol. The formulations can include additions, such as surfactants, low volatility liquids and other pharmaceutically acceptable ingredients, e.g., glycerol, propylene glycol (PG) in amounts up to 80% by volume.

Various substances can be included in the liquid formulation to produce aerosols, depending on the desired application of the liquid formulation. For example, liquid formulation can comprise a medicament that can be delivered to a patient by an aerosol. Exemplary types of medicaments that can be used include, but are not limited to, analgesics, anginal preparations, anti-allergics, antibiotics, antihistamines, antitussives, bronchodilators, diuretics, anticholinergics, hormones and anti-flammatory agents, such as those described in U.S. Pat. No. 6,153,173, which is hereby incorporated by reference in its entirety. The liquid formulation can be selected to provide a desired dose of the medicament via aerosol inhalation. The formulation can be in the form of a solution, suspension, dispersion or emulsion.

Exemplary medicaments that can be used include, but are not limited to, insulin, buprenorphine hydrochloride, cromolyn sodium, albuterol sulfate, isoproterenol sulfate, metaproterenol sulfate, terbutaline sulfate, pirbuterol acetate, salmeterol xinotoate, formotorol, beclomethasone dipropionate, flunisolide, fluticasone, budesonide, triamcinolone acetonide, beclomethasone dipropionate, triamcinolone acetonide, flunisolide and fluticasone.

However, in some embodiments the liquid formulation may not include a medicament. For example, the liquid formulation may contain another type of substance, such as a paint, scent or fuel for research, commercial, or industrial applications. Those skilled in the art will appreciate that can be important for many formulations to retain their chemical, physical and activity integrity after the process of aerosol particle formation. For example, maintaining the chemical, physical and activity integrity of polypeptide formulation such as insulin formulation can be important in many applications. Accordingly, conditions that would degrade these characteristics of the formulation should be avoided where appropriate.

Figure 1:
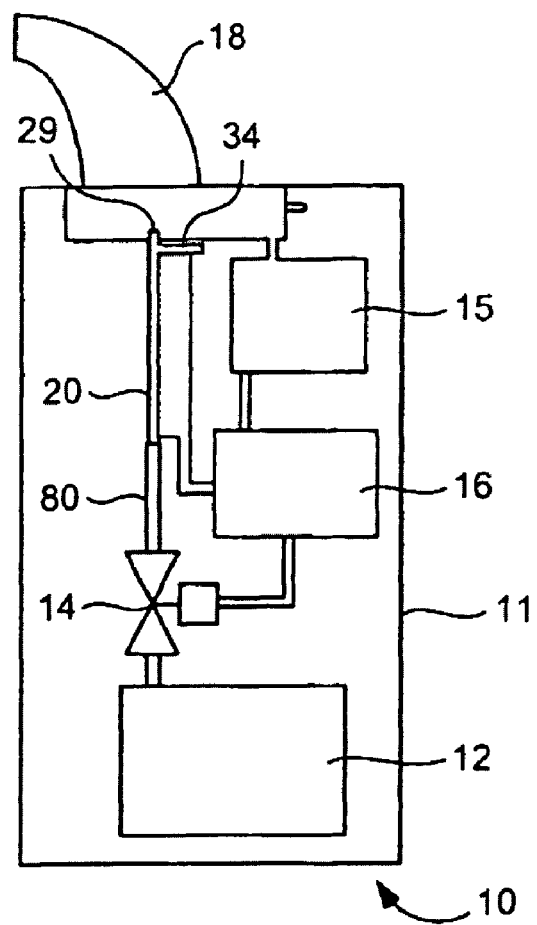
FIG. 1 illustrates an exemplary embodiment of an aerosol generator.

FIG. 1 depicts a preferred embodiment of a handheld aerosol generator 10 comprising a housing 11 and components inside the housing including a flow passage 20 and optional components including a liquid source 12, a valve 14 arranged along supply passage 80 in flow communication with the liquid source 12 and the flow passage 20, a pressure sensor 15 and a controller 16. The liquid source 12 can be removably attached to the aerosol generator 10 to allow the liquid source 12 to be replaced with another liquid source containing the same or a different liquid formulation. A mouthpiece 18 can be arranged in fluid communication with the flow passage 20. The controller 16 can include suitable electrical connections and ancillary equipment, such as a power supply (e.g., rechargeable or replaceable battery), that cooperate with the controller 16 to operate the valve 14 and sensor 15, and supply electricity to effect heating of the capillary passage 20.

To operate the aerosol generator 10, the valve 14 is opened to allow liquid to be supplied from the liquid source 12 to the flow passage 20. For example, in one preferred embodiment, liquid can be supplied to the flow passage 20 when the sensor 15 detects that a predetermined vacuum pressure has been applied to the mouthpiece 18 by a user trying to inhale aerosol from the aerosol generator 10. As liquid comprising a suspension, solution or emulsion containing a medicament or other substance is supplied from the liquid source 12 to the flow passage 20, the controller 16 controls the amount of power applied to the liquid in the flow passage 20 such that the liquid is heated to a sufficiently high temperature to volatilize at least a portion of the liquid, i.e., form a vapor. For instance, at least 10%, 20%, 30%, 40%, 50%, 60%, 70%, 80%, 90% or more of the liquid can be heated to a vapor state by the heater while in the flow passage. In another preferred embodiment, the aerosol generator 10 can be operated manually without the sensor 15 by way of a user activating a mechanical switch, electrical switch, or the like. Vapor produced by heating the liquid and entrained liquids are expelled from the outlet end 29 of the flow passage 20. The expelled vapor admixes with ambient air to form an aerosol inhaled by a user drawing upon the mouthpiece 18.

The aerosol generator shown in FIG. 1 can be modified to utilize different liquid source arrangements. In one preferred embodiment, the liquid source 12 includes a valve that is operable to deliver a predetermined volume of liquid to the flow passage 20 to produce an aerosol. In another preferred embodiment, the liquid source 12 is sized to contain a desired volume of liquid, for example, a predetermined single dose of liquid or multiple doses of the liquid. The dose is the volume of liquid that is supplied to the flow passage 20 and converted to an aerosol during one inhalation cycle. In other embodiments, the valve(s) can be omitted and the liquid source 12 can include a syringe pump, or the like, which supplies liquid to the flow passage 20.

The heater of the aerosol generator 10 is located to heat a volatilization section of the flow passage 20. The heater can include, for example, one or more walls of the flow passage 20. Such wall(s) can be made from an electrically conductive material, so that applied voltage heats the flow passage 20 and liquid contained in the flow passage. In other preferred embodiments, the flow passage can include a non-conductive or semiconductive material, such as glass or silicon, and a heater made of a resistive material, such as platinum or the like, deposited in or on a layer of material along the flow passage. Examples of heater constructions and techniques for manufacturing heater arrangements can be found in U.S. Pat. No. 6,701,922, issued Mar. 9, 2004 and U.S. patent application Ser. No. 10/648,282, filed Aug. 27, 2003, the subject matter of each being hereby incorporated by reference.

The flow passage 20 can be made of various materials, including metals, ceramics, glasses, plastics, polymers and combinations thereof. In a preferred embodiment, the flow passage 20 is defined by a capillary-sized tube of an electrically-conductive metal, for example, stainless steel or the like. Alternatively, the flow passage 20 can be of a non-conductive material (for example, a ceramic, such as alumina, a glass, or a polymer, such as KAPTON, which is a polyimide material available from E.I. du Pont de Nemours and Co., located in Wilmington, Del.) or a semi-conductive material (for example, silicon) and include a heater of an electrically conductive material, such as platinum or the like, to heat liquid in the flow passage. Ceramic materials can be formed, for example, by slip casting. Glass materials can be formed by molding. Regarding polymer materials, the flow passage can be formed by any suitable technique, such as laser ablation.

Figure 2:
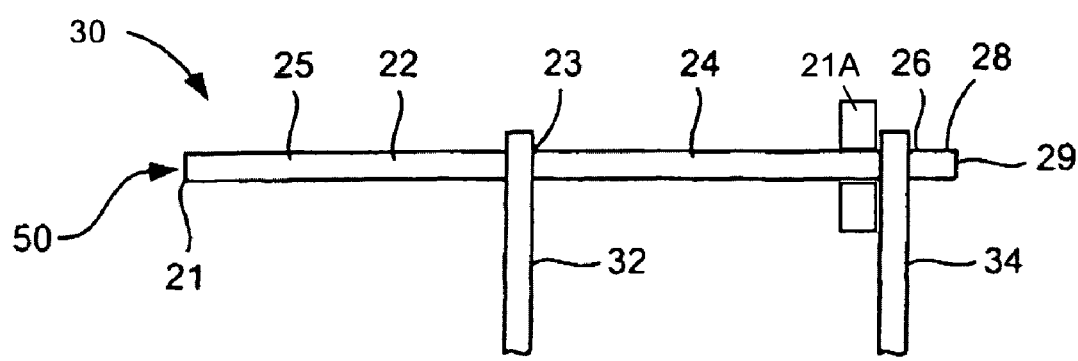
FIG. 2 is a schematic illustration of a heated capillary flow passage according to an exemplary embodiment.

FIG. 2 depicts an embodiment of a capillary aerosol generator 30 including a capillary-sized tube 25 defining a flow passage 20 having an inlet end 21 through which liquid is supplied into the flow passage, and an outlet end 29 through which vapor and liquid are expelled. In the embodiment, the flow passage 20 is unconstricted. The capillary aerosol generator 30 includes a heater having a first electrode 32 and a second electrode 34 connected to the capillary tube 25 at respective longitudinally-spaced locations 23 and 26. The electrodes 32, 34 divide the flow passage 20 into an upstream feed section 22 between the inlet end 21 and the first electrode 32, a heated section 24 between the first electrode 32 and the second electrode 34, and a downstream tip 28 between the second electrode 34 and the outlet end 29 of the capillary tube 25. Optionally, the heated section between the first electrode 32 and the second electrode 34 can include a cooling device 31 attached to the capillary tube 25. Preferably, the cooling device 31 is located in a portion of the heated section adjacent to or near the second electrode 34.

In the capillary aerosol generator 30, liquid is supplied from a liquid source 50 into the flow passage 20 of the capillary tube 25 through the inlet end 21. As the liquid is flowed through the capillary tube 25 from the feed section 22 into the heated section 24, heat is generated by applying a voltage and passing an electrical current between the first electrode 32 and second electrode 34. The applied heat is conducted to the liquid in the heated section 24. At least some of the liquid reaches a sufficiently high temperature to transform to vapor, which passes from the heated section 24 to the tip 28 and exits from the outlet end 29 of the capillary tube 25.

As liquid flows through the capillary tube 25, heat conduction to the liquid is high due to the relatively high coefficient of heat transfer between the liquid and the wall of the capillary tube 25. Heated liquid that is converted to vapor continues to move downstream along the heated section 24. Phase transition boiling occurs in the capillary tube 25 when liquid is converted to vapor, generating a pressure oscillation in the flow passage. It has been observed that when certain liquid formulations including a highly-volatile liquid, such as a highly-volatile excipient (for example, water, ethanol and mixtures thereof) and another substance (for example, a medicament), are heated in the flow passage to produce a vapor, it can be difficult to achieve reproducible delivery of an aerosol containing the medicament. Particularly, significant pressure oscillations can occur in the flow passage when such liquid formulations including a highly-volatile liquid are vaporized with the result that the desired mass median aerodynamic diameter ("MMAD") for the aerosol is not achieved. The MMAD for an aerosol is the geometric mean aerodynamic diameter of the aerosol's particles. In an aerosol, 50% of the particles by weight will be smaller than the MMAD and 50% will be larger.

Large pressure oscillations that occur in the capillary tube 25 when highly-volatile liquids are vaporized have been found to relate to shifts in the position of the liquid meniscus within the capillary tube 25. The location of the "meniscus" is defined herein as the furthest downstream location of liquid in contact with an inner surface of the wall defining the capillary tube 25. Because the heat transfer coefficient between the wall of the flow passage and vapor is low, the temperature of the wall downstream of the meniscus position can become higher than a desired maximum temperature to produce a good-quality aerosol. It has been determined that when aerosols are produced using highly-volatile liquids, such as a highly-volatile excipient, the meniscus position constantly changes within the flow passage in response to pressure changes that occur when such liquids are vaporized.

The significant pressure changes that have been determined to occur in the flow passage of the aerosol generator during the vaporization of highly-volatile liquids may produce undesirable instabilities in the performance of the aerosol generator. Namely, such pressure fluctuations cause the boiling point of highly-volatile liquids in the flow passage to change. Also, as the meniscus moves within the flow passage, fluid that originally moved toward the outlet end of the flow passage can, due to pressure fluctuations, reverse direction and move toward the inlet end of the flow passage, thereby being heated a second time in the flow passage. The reverse movement of the meniscus can create a large vapor section within the flow passage. Consequently, the buildup of solids and associated clogging within the flow passage are more likely to occur.

It has unexpectedly been determined that high-quality aerosols can be produced from liquid formulations that contain a highly-volatile liquid by providing a constriction at the outlet end of the flow passage. The constriction is configured to partially occlude the outlet end of the flow passage and decrease the cross-sectional area of the flow passage at the outlet end. The constriction defines a downstream flow section of the flow passage that has a transverse cross-sectional area that is smaller than the transverse cross-sectional area of the heated section 24, or "volatilization section," of the flow passage upstream of the constriction.

While not wishing to be held to any particular theory, the constricted flow passage is believed to produce aerosols by a fluid shearing mechanism. Particularly, during operation of the aerosol generator, vapor is produced in the heated section 24. The vapor creates high pressure and provides a driving force to expel liquid from the flow passage. Reducing the cross-sectional area at the outlet end of the flow passage increases the velocity of vapor traversing the tip and is believed to create sufficiently high shear forces to break up coarse droplets into smaller ones, which increases the efficiency of conversion of the liquid formulation to a respirable aerosol. A high vapor velocity can be achieved by either increasing the liquid flow rate in the flow passage or the amount of power that is applied to the flow passage by the heater, which increases the vapor fraction of the formulation. Liquid droplets entrained from the liquid film at the inner surface of the flow passage are suddenly exposed to a high-velocity vapor flow, resulting in a high relative velocity between the droplet and the vapor. It is hypothesized that the shear created by this velocity differential creates a Kelvin-Helmholtz instability that causes the break up of the droplets. The droplet size above which such break up can be expected to occur is a function of the dynamic pressure, surface tension and viscous forces. For liquids of low viscosity, such as 100% water formulations, the deformation of a droplet is determined primarily by the ratio of the aerodynamic force to the surface tension force, which is given by the dimensionless Weber number=$(\rho_{vap} U^2_{R,vap} D)/\sigma$, where $\rho_{vap}$ is the vapor density, $U_{R,vap}$ is the relative velocity between the droplet and the vapor, D is the droplet diameter, and $\sigma$ is the surface tension of the liquid. It is generally accepted that, for low viscosity liquid droplets suddenly exposed to a high velocity air stream, the critical value of the Weber number is about 13. Using this value, the smallest or critical droplet diameter that can be broken up in a high-speed, compressible gas flow can be calculated.

Figure 3:
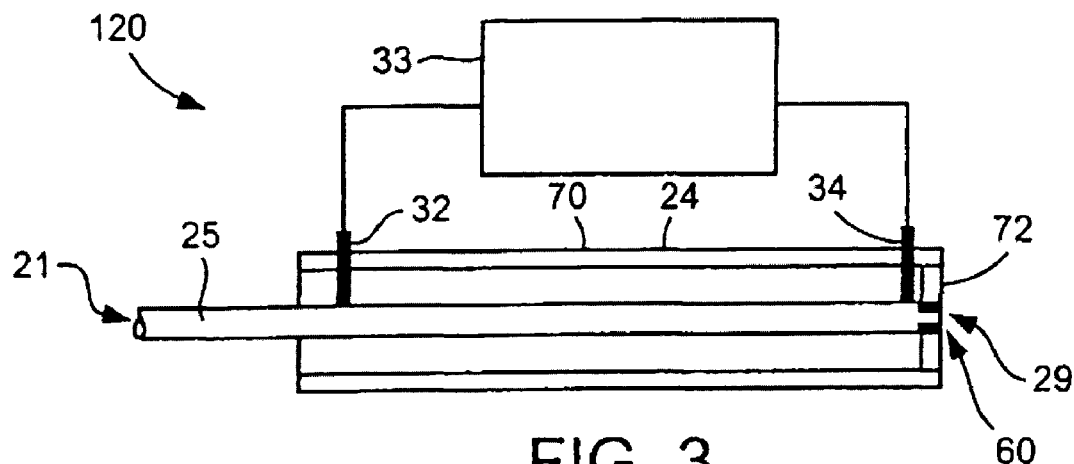
FIG. 3 shows a preferred embodiment of an aerosol generator.

As shown in FIG. 3, a preferred embodiment of an aerosol generator 120 includes a capillary-sized capillary tube 25, such as a capillary tube having an inlet end 21, an outlet end 29, and a constriction 60 at the outlet end 29. The aerosol generator 120 also includes a heater having a first electrode 32 and a second electrode 34 connected to the capillary tube 25 and to a power supply 33. The electrodes 32, 34 define a heated section 24 between the first electrode 32 and the second electrode 34, and a downstream tip between the second electrode 34 and the outlet end 29 of the capillary tube 25. In a preferred embodiment, the capillary tube 25 has an inner diameter of about 0.025 mm to about 0.5 mm, more preferably about 0.025 mm to about 0.25 mm, or about 0.1 mm to about 0.2 mm, and the heated section 24 preferably has a length of about 5 mm to about 40 mm, more preferably about 15 mm to about 25 mm, for preferred liquid flow rates of about 5 µL/sec to about 30 µL/sec.

The aerosol generator 120 can optionally include a sleeve 70 surrounding the capillary tube 25 to control heat transfer to and from the capillary tube, and an end cap 72 at the outlet end 29 to prevent material expelled from the flow passage from flowing back into the space surrounding the capillary tube 25.

Figure 4:
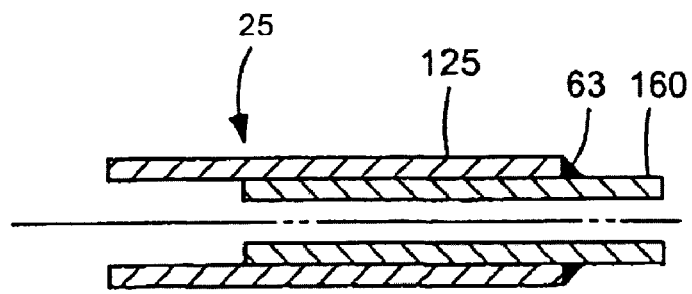
FIG. 4 is a cross-sectional view of a preferred embodiment of a flow passage including a constriction in the form of an insert having a reduced cross-section at the outlet end.

In a preferred embodiment, the constriction is an insert 160 in the flow passage at the outlet end 29, as depicted in FIG. 4.

The capillary tube 25 and the insert 160 can be of the same material or a different material. The material can be selected from metals, ceramics, glasses, plastics, polymers and combinations thereof. The insert 160 can have a length of, for example, about 1 mm to about 10 mm, more preferably about 3 mm to about 6 mm. In embodiments of the insert 160 having a circular open cross-section, the inner diameter of the insert 160 is preferably about 0.001 in (about 25 µm) to about 0.01 in (about 250 µm), more preferably from about 0.001 in (about 25 µm) to about 0.003 in (about 75 µm). The ratio of the cross-section of the flow passage to the open cross-section of the constriction can be, for example, about 2:1 to up to about 30:1. This ratio can also be provided for other configurations of the constriction, such as those configurations described below. For inserts 160 having a circular or a non-circular open cross-section, the open cross-sectional area of the insert 160 is preferably about 500 µm$^2$ to about 51,000 µm$^2$, more preferably about 500 µm$^2$ to about 8,000 µm$^2$, still more preferably about 500 µm$^2$ to about 3,000 µm$^2$ or about 500 µm$^2$ to about 1,000 µm$^2$. These insert dimensions are preferably for liquid flow rates of about 5 µL/sec to about 30 µL/sec. At higher flow rates, the cross-sectional area of the inner diameter of the insert can be increased.

As shown in FIG. 4, the insert 160 can be bonded to the flow passage 20 by a joint 63 formed by any suitable technique depending on the materials of the capillary tube 25 and insert 160. In a preferred embodiment, the flow passage 20 and insert 160 are of the same or a different metallic material, and can be joined, for example, by welding, soldering or brazing.

Figures 5, 6:
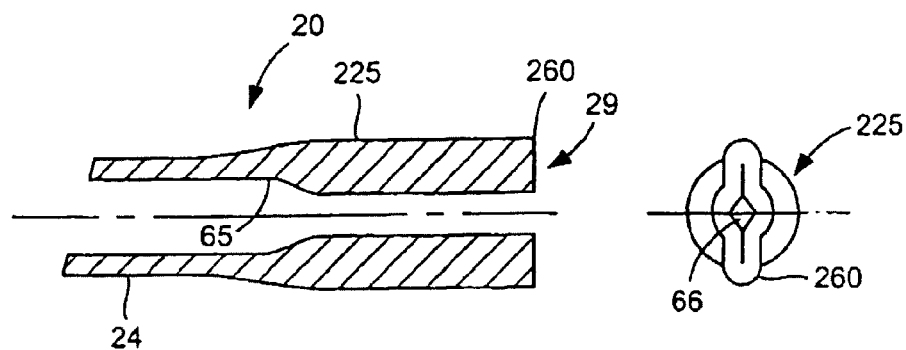
FIG. 5 is a cross-sectional view of another preferred embodiment of a flow passage including a constriction in the form of a formed tip having a reduced cross-section at the outlet end.
FIG. 6 is a front elevation view of the flow passage shown in FIG. 5.
Figure 7:
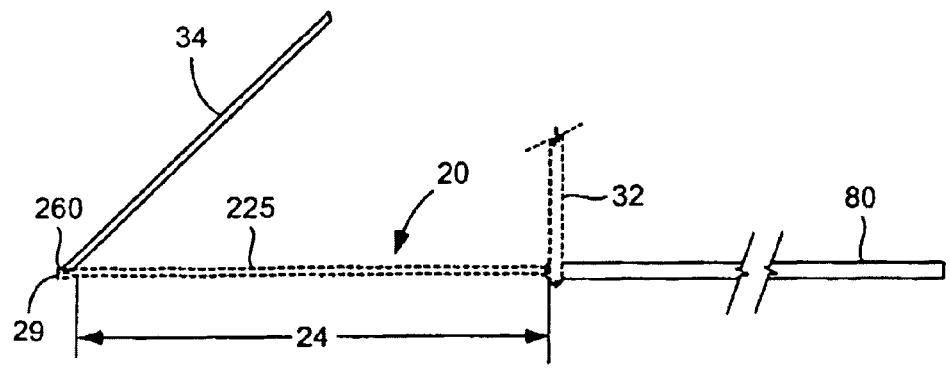
FIG. 7 illustrates a heated flow passage including the flow passage shown in FIG. 5.

As shown in FIGS. 5-7, in another preferred embodiment of the aerosol generator, the capillary tube 225 can include a constriction in the form of a formed tip 260 at the outlet end of the flow passage 20. The formed tip 260 includes a flow section 66. The formed tip 260 can be formed by any suitable technique. For example, the formed tip 260 can be formed by inserting a mandrel, such as a cylindrical wire, a desired distance into the flow passage 20, and then deforming the capillary tube 225 around the mandrel, such as by crimping. The mandrel can have a desired cross-sectional shape and cross-sectional area that define the desired size and shape of the flow section 66. In a preferred embodiment, the mandrel is a solid cylindrical wire and the flow section 66 has a circular or substantially circular cross-section. As shown in FIG. 5, the inner surface of the capillary tube 225 includes a tapered surface 65 between the inner surface defining the heated section 24 and the formed tip 260. The tapered surface 65 can have any suitable contour.

In one embodiment, a tipped capillary tube 225 can be made from a 35 mm length of K32EG tubing (304 stainless steel tubing with an internal diameter of about 0.0075 inches and outside diameter of about 0.0009 inches—available from K Tube Corporation, Poway, Calif.). In this embodiment, electrode 34 is a 0.012 inch or 0.013 inch stainless steel wire of about 9 mm in length. By altering the material and geometry of electrode 34, the temperature of the capillary can be changed. The tip 260 is fabricated by forming the capillary tube 225 around a 0.002 inch diameter tungsten wire giving a finished open area of about 2600 µm$^2$.

In yet another embodiment, the tip 260 of the capillary tube 225 can be formed by welding closed an end of the capillary tube to form a domed closure. An opening is then made in the domed closure by drilling or laser cutting a hole of desired smaller diameter. Alternatively, a tipped capillary can be formed by attaching a metal cap to one end of a capillary by press fitting the cap to the capillary or by welding the cap in place. Either before or after attaching the cap to the capillary, a laser can be used to drill an orifice in the metal cap of a diameter that is less than the capillary's inner diameter. The orifice size can be controlled by adjusting the laser spot diameter, the laser mask diameter and the laser's energy density. A benefit of this method of manufacture is the ability to accurately control the exit dimensions of the resulting tipped capillary through which the expelled vapors and liquids flow. These dimensions can affect the resulting particle size, velocity and spray angle of aerosol. This method is also reliable and commercially scalable.

Another method for forming a tipped capillary by electrolytic deposition of layers of metal within a capillary tube. Preferably, the capillary tube is stainless steel. This method involves dipping a desired length the capillary tube into an appropriate electrolyte solution and electroplating the dipped length with metal. Optionally, the outer dipped surfaces of the capillary tube can be coated or masked to prevent deposition on the outer surfaces of the tube. Alternatively, the outer surfaces can be abraded or machined to remove unwanted deposited metal.

The formed tip 260 of the flow passage 20 can have a length of, for example, about 0.5 mm to about 3 mm. In embodiments of the capillary tube 225 in which the formed tip 260 includes a flow section 66 having a circular open cross-section, the diameter of the flow section 66 is preferably about 0.001 in to about 0.01 in, more preferably about 0.001 in to about 0.003 in. For flow sections 66 having a circular or a non-circular cross-section, the cross-sectional area of the flow section 66 is preferably about 500 $\mu m^2$ to about 51,000 $\mu m^2$, more preferably about 500 $\mu m^2$ to about 8,000 $\mu m^2$. These formed tip dimensions are preferably for liquid flow rates of about 5 µL/sec to about 30 µL/sec.

Figures 8, 9:
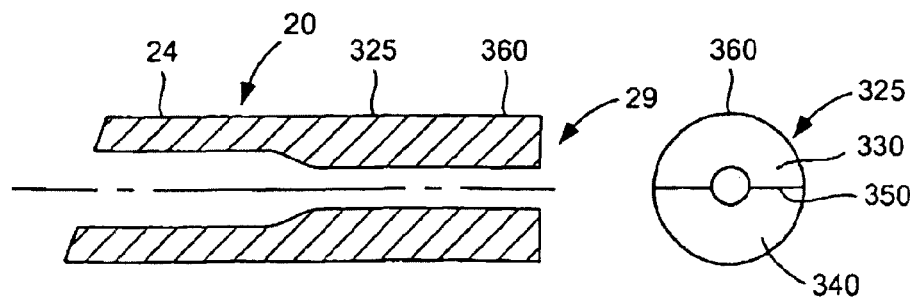
FIG. 8 is a cross-sectional view of another preferred embodiment of a flow passage including a two-piece constriction having a reduced cross-section at the outlet end.
FIG. 9 is a front elevation view of the flow passage shown in FIG. 8.

FIGS. 8 and 9 depict another preferred embodiment of the aerosol generator. In this embodiment, the capillary flow passage can be a one-piece monolithic body 325 including a constriction 360 defining a flow section 366 at the outlet end 29 of the flow passage 20. In such embodiments, the monolithic body can be formed, for example by a molding process. The flow section 366 can have a circular or non-circular shape.

In another preferred embodiment, the capillary flow passage can be a laminated structure. For example, the laminated structure can include a piece having a surface in which a groove or channel is formed, and another piece that is adapted to cover the groove or channel to define the flow passage. The flow passage in the laminated structure includes a constriction at the outlet end. The constriction can be formed by reducing the depth of the groove or channel at the outlet end, as compared to the portion of the groove or channel upstream of the outlet end.

During operation of the aerosol generator 120, liquid is supplied to the inlet end 21 of the capillary tube 25 from a liquid source. Electrical current is passed through the tube 25, such that the heater is activated to heat the liquid in the heated section 24 of the flow passage 20 such that at least some of the liquid is converted into vapor. The vapor, as well as liquid that may not be volatilized in the heated section 24, are expelled from the flow passage via the flow section defined by the constriction 60.

The aerosol produced by the aerosol generator can be characterized in different ways. Particularly, the aerosol quality can be characterized by the particle size distribution of the aerosol, and/or the recovery of one or more components of the aerosol. Regarding the particle size distribution, the mass of aerosol particles having a size less than some selected size can be the basis for characterization of the aerosol. The selected particle size can be, for example, a certain size that facilitates deep lung penetration. For example, the aerosol can have an MMAD of less than 10 µm, preferably about 0.01 µm to about 1 µm, or about 1 µm to about 3 µm or about 1 µm to about 5 µm.

Aerosol delivery can alternatively be characterized by the emitted dose, and/or the respirable dose, of one or more component(s) of an aerosol. The component(s) can be one or more medicaments, for example. The emitted dose is the ratio of the mass of the component(s) emitted by the fluid vaporizing device to a metered dose of the component(s) supplied to the capillary passage (i.e., emitted dose=[mass of component(s) emitted/metered dose]×100). The respirable dose is the ratio of the mass of aerosol particles smaller than a selected size, x, to the emitted dose (i.e., respirable dose= [mass of aerosol particles<x/emitted dose]×100).

Comparative tests were conducted to determine capillary aerosol generator heater (CAG heater) performance characteristics for exemplary capillary-sized flow passage heaters. The CAG heaters were used to aerosolize a liquid.

Capillary aerosol generators can suffer from clogging during operation. Certain formulations used in capillary aerosol generators, for example, insulin formulations, can be particularly prone to clogging. Unexpectedly, it has been found that cooling areas of a capillary tube near the outlet of an aerosol generator, such as the capillary aerosol generator 30 depicted in FIG. 2, can alleviate clogging. Cooling can be achieved by attaching any one or more of a variety of cooling devices 21A at or near the outlet 29 of the capillary tube 25 to avoid overheating or excessively drying out the heated formulation. Overheating or excessive drying of the formulation may occur causing deposition of solids in the portions of the capillary tube at the downstream end of the heated section 24 and near the tip 28. Although cooling devices can be located downstream of the heated section 24 and electrode 34, as depicted in FIG. 2, a cooling device 21A can advantageously be located upstream of electrode 34. In particular, the cooling device 21A is preferably located along the downstream half of heated section 24, but upstream of and near or adjacent to electrode 34. The cooling device preferably reduces the temperature of the section of the capillary tube 25 to which it is attached by about 10° C. to about 100° C. when compared to a capillary aerosol generator 30 operating without the cooling device. More preferably, the cooling device reduces the temperature of the cooled section by about 30° C. to about 85° C. and even more preferably by about 50° C. to about 70° C.

According to one alternative, cooling is achieved by locating a heat sink at or near the tip 28 of the capillary tube 25, attached to a downstream portion of the heated section 24 adjacent to electrode 34. Suitable heat sinks can be in the form of a mass of conductive material in contact with the capillary tube 25, and shaped and sized to achieve a desired rate of heat dissipation from the contacted portion of the capillary tube 25 as heated fluid is expelled. Factors that may affect the mass and shape of the heat sink or, indeed, the desired performance of cooling devices in general can include: the temperature and quantity of heat stored in the fluid being expelled through flow passage 20, the rate of fluid flow through the flow passage 20, the time between uses of the capillary aerosol generator 30 when no fluid is being ejected, and the ambient temperature.

In an exemplary capillary aerosol generator 30, the cooling device is a heat sink attached to a section of capillary tube 25 upstream and adjacent to electrode 34. In this embodiment, the heat sink is made from a brass disk having an outer diameter of about 0.4 inches and thickness of about 0.009 inches and a metallic washer having an outer diameter of about 0.25 inches an internal diameter of about 0.1 inches and a thickness of about 0.035 inches. The metallic washer can be made from steel. The two disks are joined to one another, preferably by brazing. In this case, electrode 34 can be brazed to the downstream face of the brass disk and a hole drilled through the electrode and brass disk through which capillary tubing 25 extends.

EXAMPLE 1

Tests were conducted to evaluate the influence on aerosol production of installing an insert in the flow passage of a CAG heater for producing aerosols from different liquid formulations including a high-volatility carrier, i.e., ethanol/water. The evaluation was conducted by comparing the performance of a CAG heater with no constriction untipped CAG) to that of a CAG heater having a constriction (tipped CAG). The CAG heater included a flow passage of K32EG tubing with an inner diameter of about 0.006 in (about 150 microns), a cross-sectional flow area of about 18,000 micron$^2$ and a length of 35 mm. The CAG heater did not include a sleeve or cap.

Figure 10:
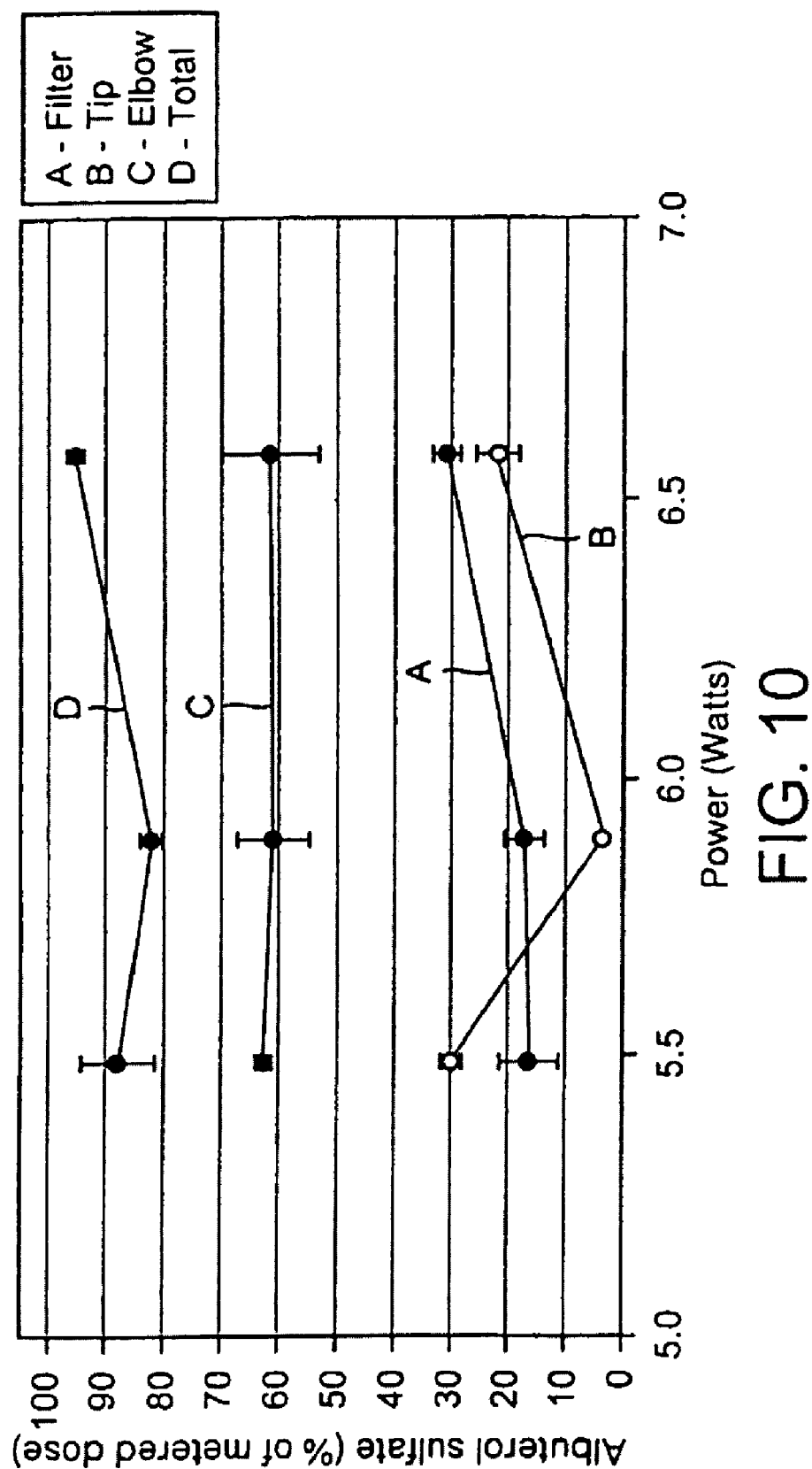
FIG. 10 shows the relationship between % recovery of albuterol sulfate aerosol particles and power applied to the heater of an aerosol generator for an aerosol produced from a liquid formulation containing 1% albuterol sulfate in 80% ethanol/20% water.

In a test, a liquid formulation containing 1% albuterol sulfate in 80% ethanol/20% water was supplied to the flow passage at a flow rate of 5 µL/sec. The % of actual metered dose of the albuterol sulfate recovered versus the applied power to the CAG heater was determined. The aerosol particles were collected using a particle collector including an L-shaped tube (elbow) in fluid communication with the outlet end of the flow passage, and a filter at the outlet end of the elbow. The "total" recovery" represents the total amount of material deposited on the tip of the flow passage, the elbow and the filter. The tip recovery is the liquid material remaining on the tip of the flow passage and was not aerosolized. The elbow recovery is from relatively large particles that correspond to particle sizes which would likely be caught in a user's throat. The filter recovery is the aerosol that would reach a user's lungs. Accordingly, it is desirable to achieve a high % aerosol recovery on the filter, and not on the tip and/or elbow. As shown in FIG. 10, the % recovery on the filter reached a maximum of about 30%, and the total % recovery ranged from about 88% to about 95% over the applied power range.

Figure 11:
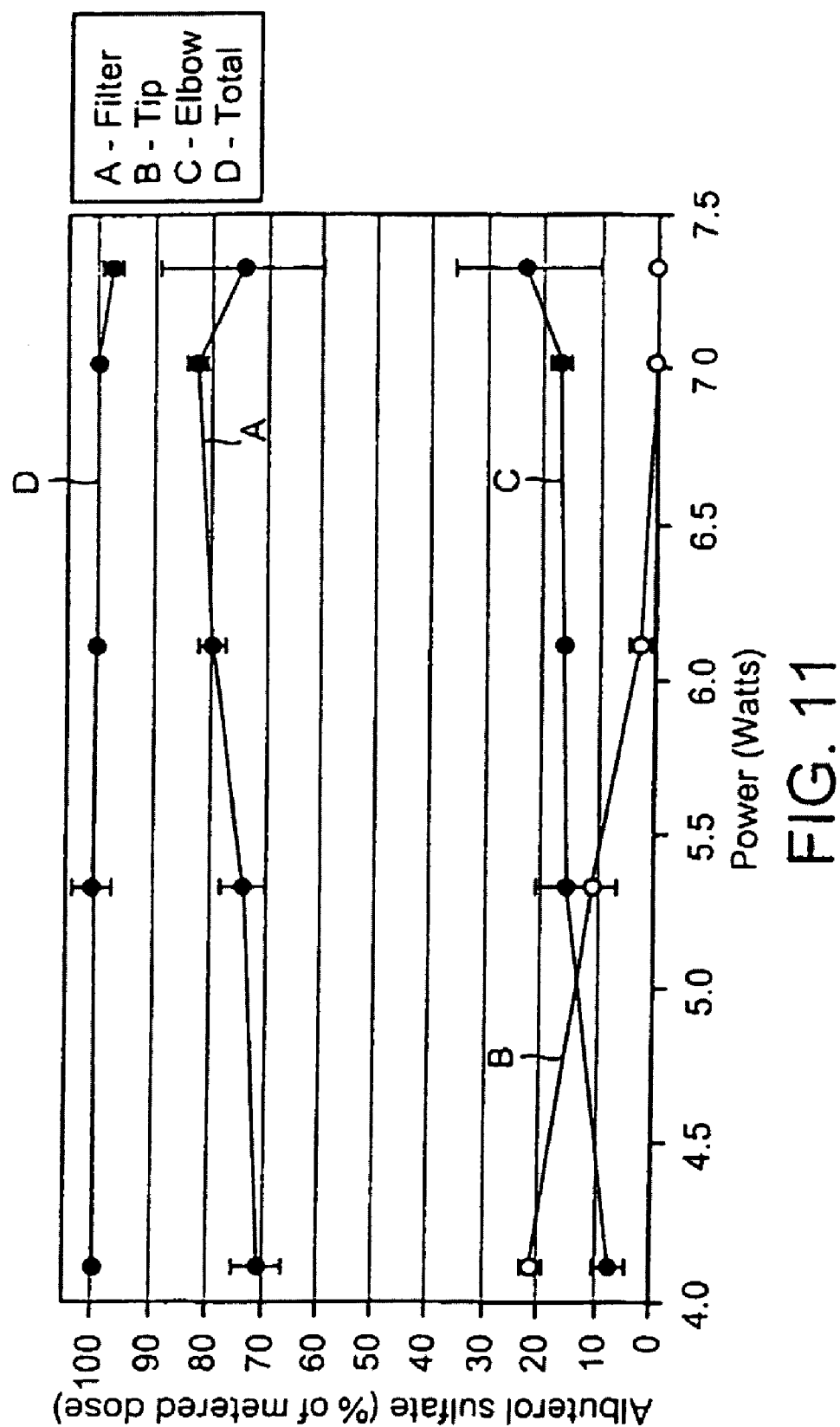
FIG. 11 shows the relationship between % recovery of albuterol sulfate aerosol particles and power applied to the heater of an aerosol generator including a flow passage having an insert at the outlet end for an aerosol produced from a liquid formulation containing 1% albuterol sulfate in 80% ethanol/20% water.

In a comparative test, the CAG heater was modified to include a constriction by placing a 35 gauge tube insert with an inner diameter of 0.002 in (about 51 microns) and a cross-sectional flow area of 2027 micron$^2$ in the flow passage at the outlet end. As shown in FIG. 11, as compared to FIG. 10, recovery was improved by the insert as the % recovery on the filter ranged from about 71% to about 83%, and the total % recovery was about 100% over the applied power range.

Figure 12:
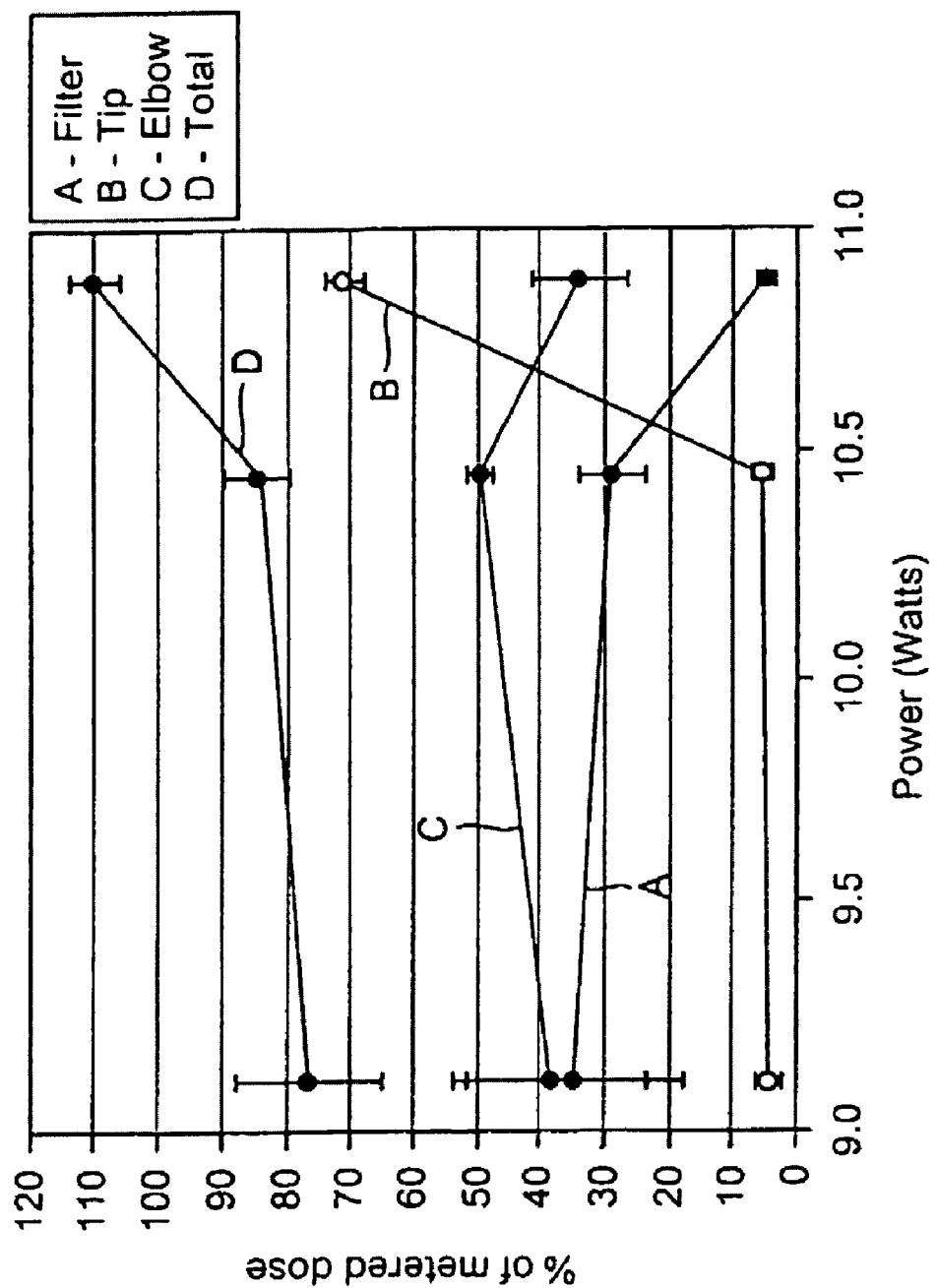
FIG. 12 shows the relationship between % recovery of cromolyn sodium aerosol particles and power applied to the heater of an aerosol generator for an aerosol produced from a liquid formulation containing 1% cromolyn sodium in 80% ethanol/20% water.

In another comparative test, an unconstricted CAG heater was used to aerosolize cromolyn sodium, which is used for the treatment of asthma. A liquid formulation containing 1% cromolyn sodium in 40% ethanol/60% water was supplied to the flow passage at a flow rate of 5 µL/sec. As shown in FIG. 12, the maximum % recovery on the filter was about 35% over the applied power range.

Figure 13:
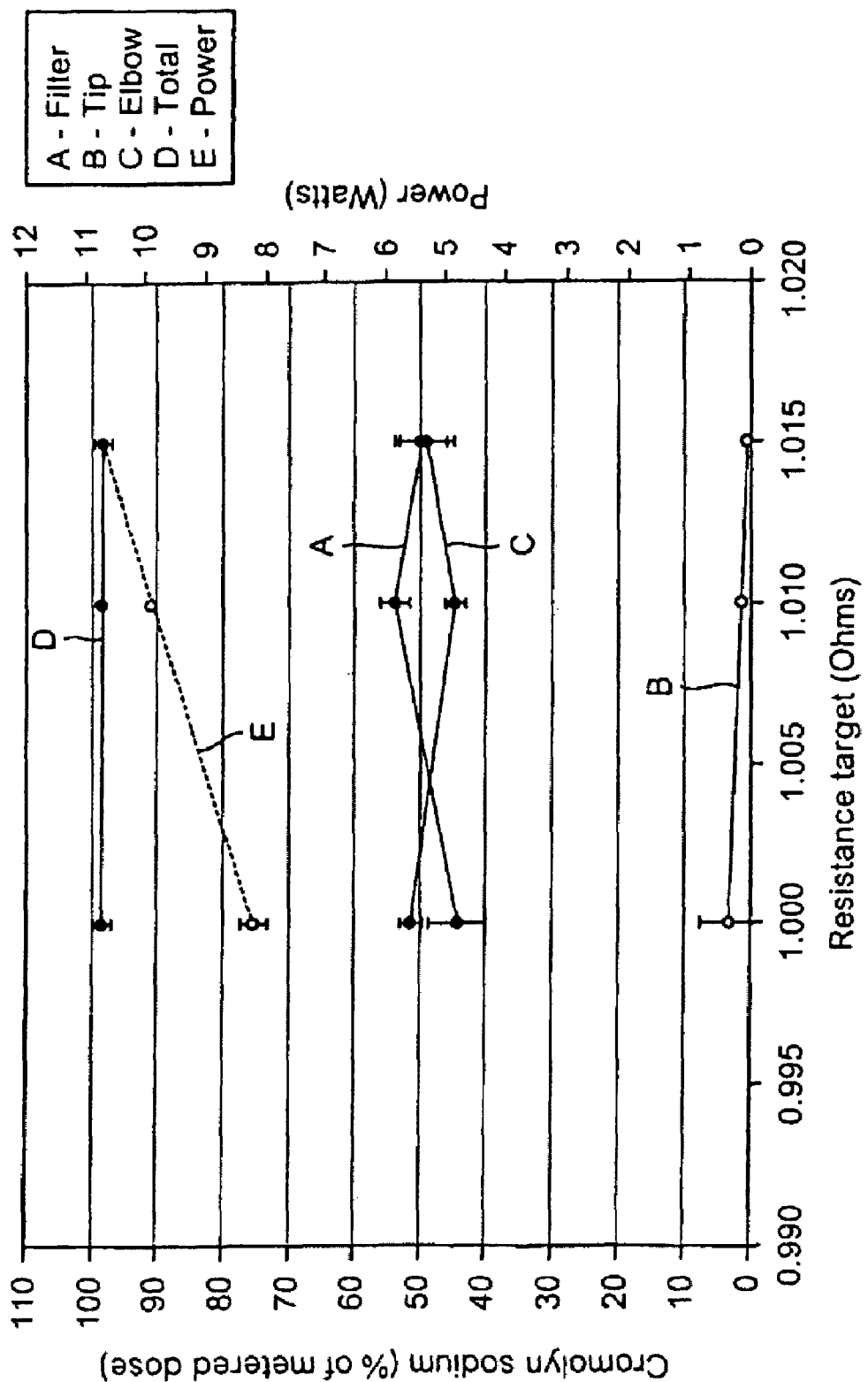
FIG. 13 shows the relationship between % recovery of cromolyn sodium aerosol particles and power applied to the heater of an aerosol generator including a flow passage having a constriction in the form of an insert at the outlet end for an aerosol produced from a liquid formulation containing 1% cromolyn sodium in 80% ethanol/20% water.

In another test, the same cromolyn sodium formulation was supplied to the flow passage of a CAG heater including a 35 gauge tube insert at a flow rate of 5 µL/sec. The test results are shown in FIG. 13. Comparing the results shown in FIG. 12, it can be seen that the insert improved the aerosol recovery, as the % recovery on the filter ranged from about 44% to about 54%, and the total % recovery was about 99% over the applied power range.

Figure 14:
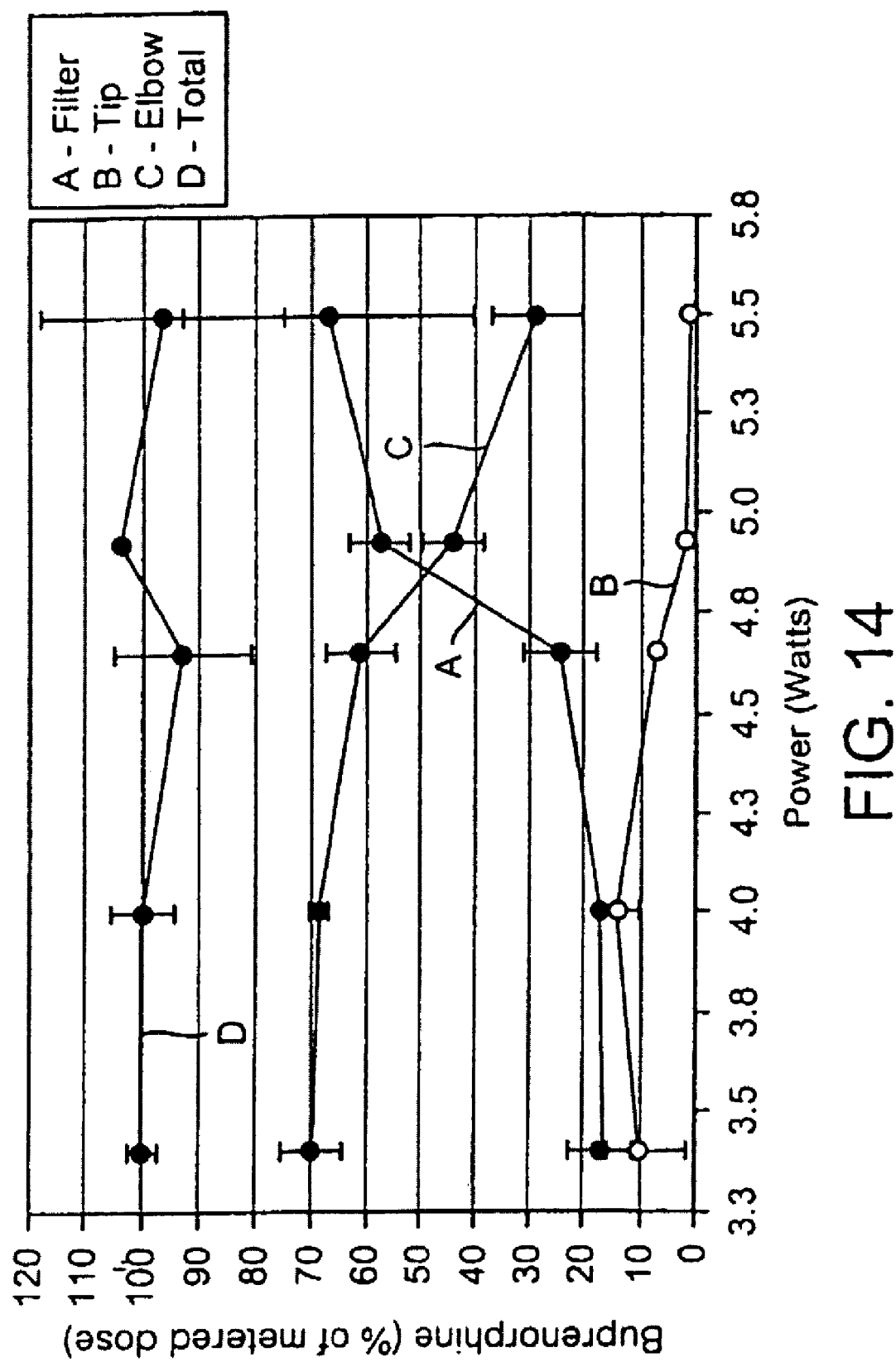
FIG. 14 shows the relationship between % recovery of buprenorphine hydrochloride aerosol particles and power applied to the heater of an aerosol generator for an aerosol produced from a liquid formulation containing 1.5% buprenorphine hydrochloride (HCl) in an ethanol/water mixture.

A further comparative test was conduced with a medicament used for the treatment of pain. A liquid formulation containing 1.5% buprenorphine hydrochloride (HCl) in an ethanol/water mixture was aerosolized using an unconstricted CAG heater. As shown in FIG. 14, the maximum % recovery on the filter was near 70% and total recoveries of at least 100% were achieved.

Figure 15:
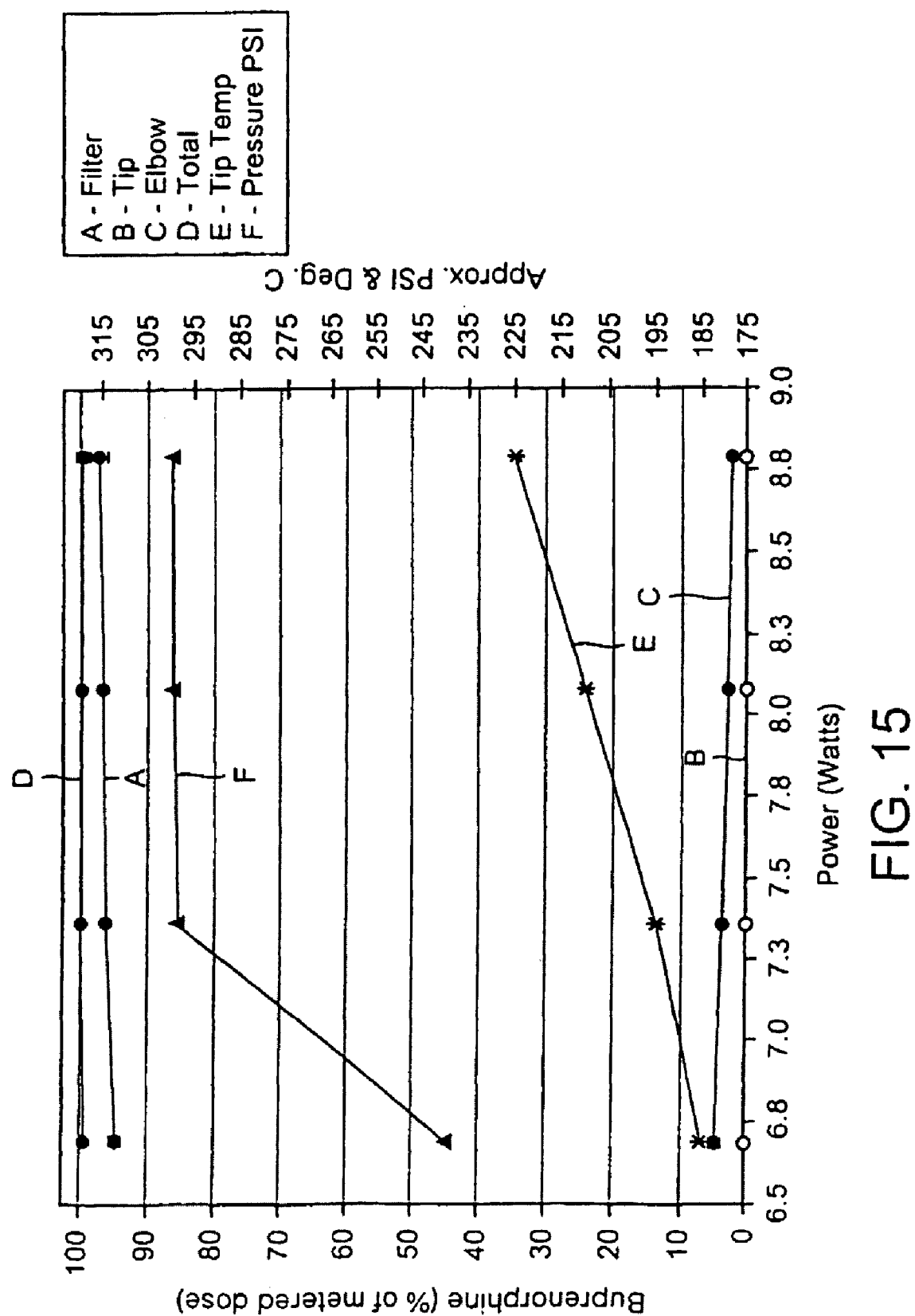
FIG. 15 shows the relationship between % recovery of buprenorphine HCl aerosol particles and power applied to the heater of an aerosol generator including a flow passage having an insert constriction at the outlet end for an aerosol produced from a liquid formulation containing 1.5% buprenorphine HCl in an ethanol/water mixture.

In another test, the same buprenorphine HCl liquid formulation was used with a CAG heater including a constriction in the form of a 35 gauge tube insert. The test results are shown in FIG. 15. Comparing these results to those shown in FIG. 14, it can be seen that the constriction improved the aerosol recovery, as the % recovery on the filter was at least about 95%, and the total recovery was about 100% over the applied power range.

EXAMPLE 2

Tests were conducted to evaluate the influence on aerosol recovery of varying the length of the flow passage of the CAG heater. The CAG heater included a flow passage with a constriction in the form of a 35 gauge tube insert at the outlet end. The CAG heater did not include a shield or cap. A liquid formulation containing 1.5% buprenorphine HCl in 95% ethanol/5% water was supplied to the flow passage at a flow rate of 10 µL/sec.

Figure 16:
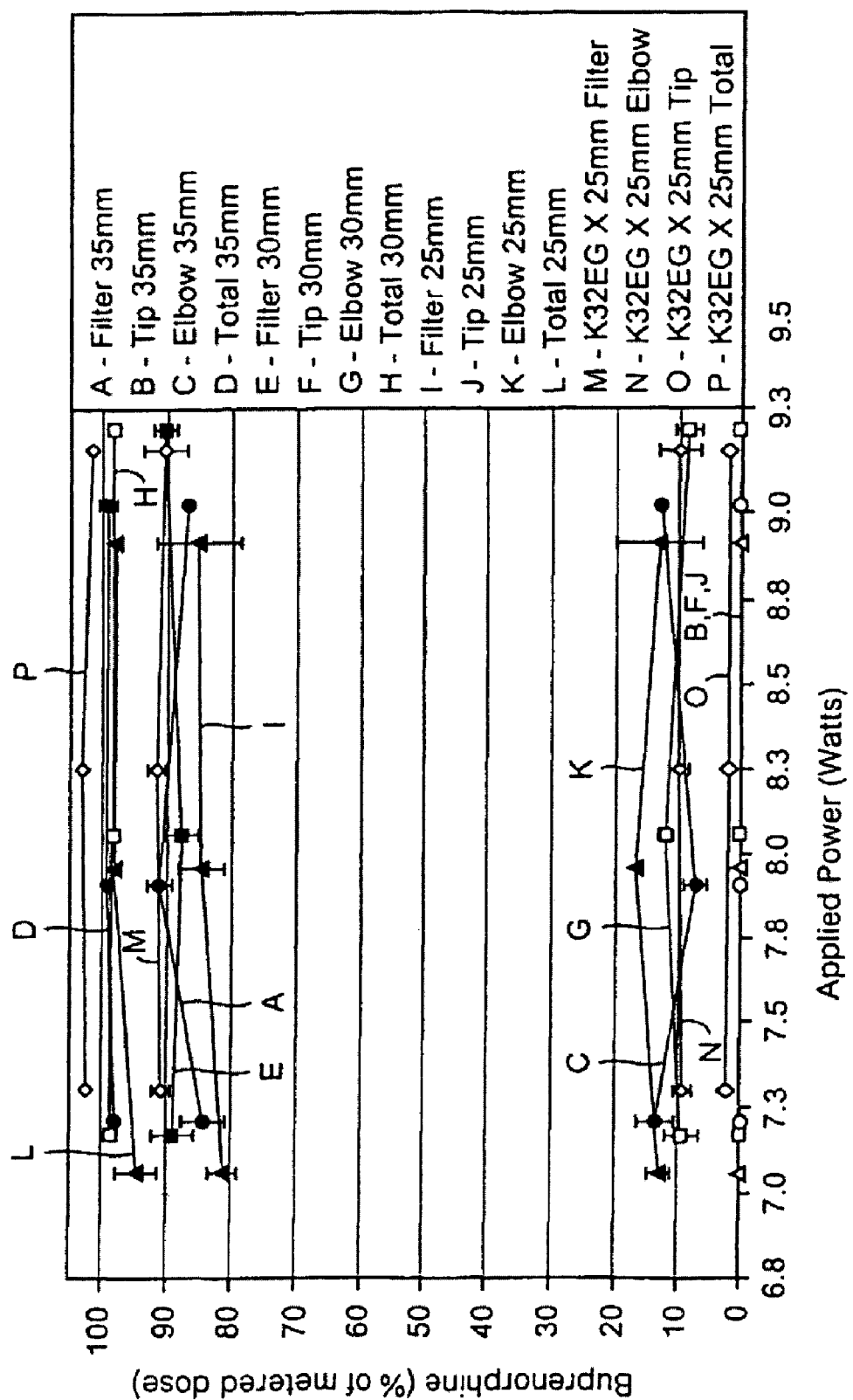
FIG. 16 shows the relationship between % recovery of buprenorphine HCl aerosol particles and power applied to the heater of an aerosol generator including a flow passage having an insert constriction at the outlet end for an aerosol produced from a liquid formulation containing 1.5% buprenorphine HCl in an 95% ethanol/5% water for capillary tube lengths of 25 mm, 30 mm and 35 mm.

In a first series of tests, the flow passage was a 30 gauge capillary tube having an inner diameter of about 0.006 in and a cross-sectional flow area of about 18,000 µm$^2$. Different capillary tube lengths of 25, 30 and 35 mm were tested. In a second test, the flow passage was of K32EG tubing having a length of 25 mm. The test results for the % of actual metered dose of the buprenorphine HCl recovered versus the applied power to the CAG heater for the different capillary passage lengths are shown in FIG. 16. The % buprenorphine HCl recovery on the filter ranged from over 80% to over 90%, and the total % recovery was up to about 100% over the applied power range. These test results demonstrate that for CAG heaters including a constricted capillary flow passage, high aerosol recoveries can be achieved for a range of flow passage lengths, and over a range of applied power levels.

EXAMPLE 3

Figure 17:
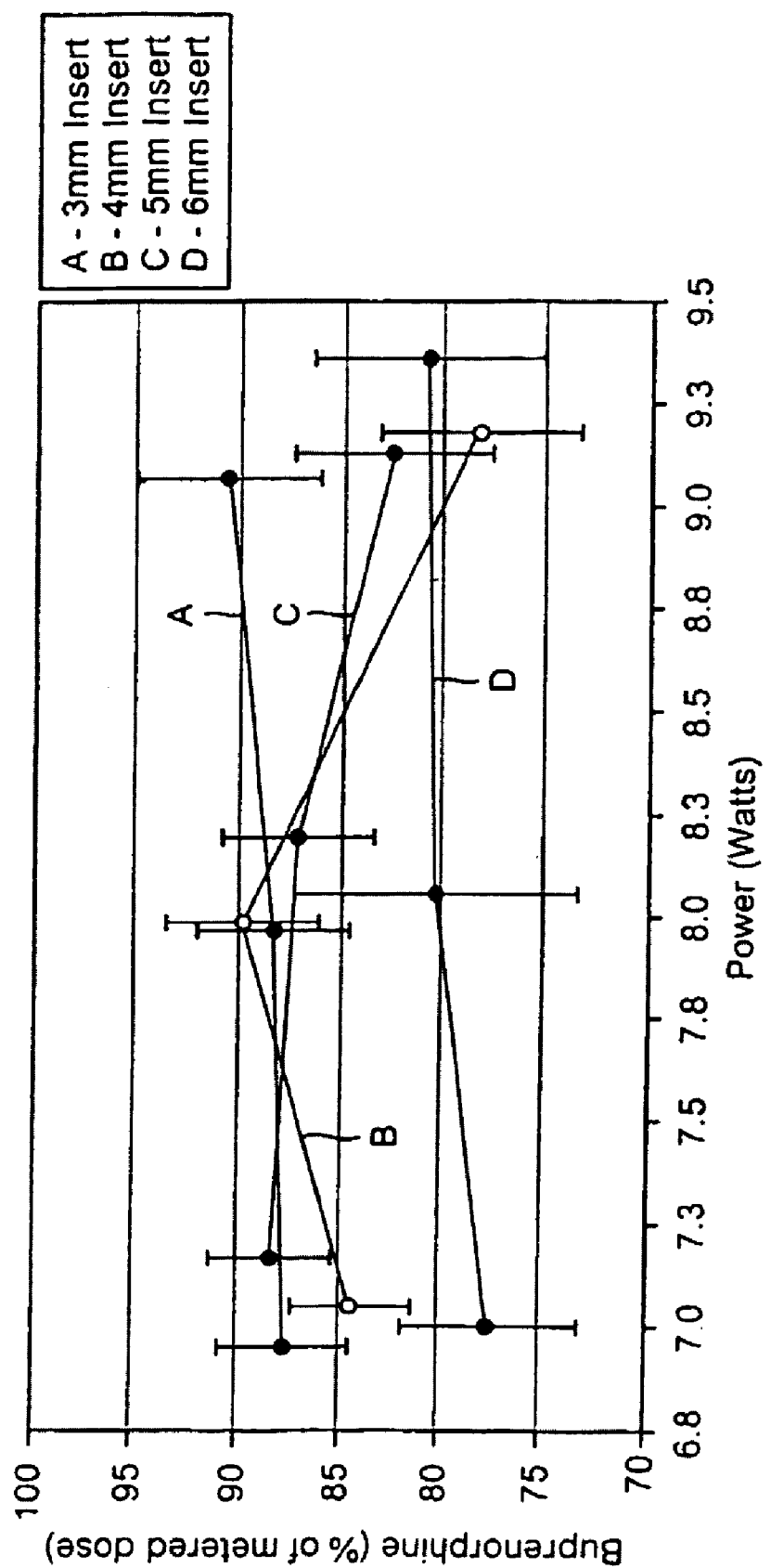
FIG. 17 shows the relationship between % recovery of buprenorphine HCl aerosol particles and power applied to the heater of an aerosol generator including a flow passage having an insert constriction at the outlet end for an aerosol produced from a liquid formulation containing 1.5% buprenorphine HCl in an 95% ethanol/5% water for different insert lengths of 3 mm, 4 mm, 5 mm and 6 mm.

Tests were conducted to evaluate the influence on aerosol production of varying the length of the constriction of the CAG heater. The CAG heater included a flow passage of K32EG tubing having a length of 35 mm. Constrictions in the form of 35 gauge tube inserts having lengths of 3 mm, 4 mm, 5 mm and 6 mm were separately installed at the outlet end of the flow passage. The CAG heater did not include a sleeve or cap. A liquid formulation containing 1.5% buprenorphine HCl in 95% ethanol/5% water was supplied to the flow passage at a flow rate of 10 µL/sec. FIG. 17 shows the test results for the % of actual metered dose of the buprenorphine HCl recovered on a filter versus the applied power to the CAG heater. The % recovery on the filter was at least about 78% for the different insert lengths. The recovery was not significantly changed by increasing the constriction length. These test results demonstrate that CAG heaters including a constriction in the capillary flow passage can provide high aerosol recoveries over a range of constriction lengths, and over a range of applied power levels.

The "cold pressure" within the capillary flow passage, i.e., the liquid pressure in the flow passage with the CAG heater turned off, was determined for each of the insert lengths using a liquid containing 95% ethanol/5% water. The highest cold pressure was measured for the 6 mm long insert, and the lowest cold pressure for the 3 mm long insert.

EXAMPLE 4

Tests were conducted to evaluate the influence on aerosol production of varying the open area of the formed tip constriction of the CAG heater. The CAG heater included a flow passage of K32EG tubing having a length of 35 mm. A liquid formulation containing 1.5% buprenorphine HCl in 95% ethanol/5% water was supplied to the flow passage at a flow rate of 10 μL/sec. Capillary flow passages having formed tip constrictions with respective open cross-sectional areas of 894 μm$^2$, 2013 μm$^2$, 3257 μm$^2$, 4967 μm$^2$ and 6798 μm$^2$ were tested. As shown in FIG. 18, the % buprenorphine HCl recovery on the filter was highest for the constriction having the smallest open cross-sectional area, and was lowest for the constriction having the largest open cross-sectional area.

The cold pressure within the capillary flow passage was determined for each capillary flow passage having a formed tip constriction using a liquid containing 95% ethanol/5% water. The cold pressure was found to decrease as the open cross-sectional area of the constriction increased. The highest cold pressure was measured for the constriction having the smallest open cross-sectional area, and the lowest cold pressure for the constriction having the largest open cross-sectional area.

The "hot pressure" within the capillary flow passage, i.e., the fluid pressure in the flow passage with the CAG heater turned on to heat the flow passage, was determined for each of the capillary flow passages having a formed tip constriction. The liquid used contained 95% ethanol/5% water. The test results revealed that the hot pressure decreased as the open cross-sectional area increased, and the hot pressure increased as the applied power was increased over the range of 7 to 9 watts.

EXAMPLE 5

Tests were conducted to evaluate the influence on aerosol production of varying the flow rate of the liquid formulation in the flow passage of the CAG heater. The CAG heater included a flow passage having a formed tip constriction. Different open cross-sectional areas of the constriction were tested. In a first test, the CAG heater included a flow passage of K32EG tubing having a length of 35 mm and a formed tip constriction with a open cross-sectional area of 6798 μm$^2$. A liquid formulation containing 1.5% buprenorphine HCl in 95% ethanol/5% water was supplied to the flow passage at flow rates of 10 μL/sec and 20 μL/sec. The observed operating pressure was increased with the increase of flow rate from an average of about 55 psi to about 120 psi with the increase in flow rate. As shown in FIG. 19, for the liquid flow rate of 10 μL/sec, the % buprenorphine HCl recovery on the filter was about 70%, and the total recovery was about 100%. As shown in FIG. 20, for the liquid flow rate of 20 μL/sec, the % buprenorphine HCl recovery on the filter was increased to about 80%, and the total recovery was about 100%.

In another test, the CAG heater included a flow passage of K32EG tubing having a length of 35 mm and a formed tip constriction with a open cross-sectional area of 4968 μm$^2$. A liquid formulation containing 1.5% buprenorphine HCl in 95% ethanol/5% water was supplied to the flow passage at flow rates of 10 μL/sec and 20 μL/sec. The observed operating pressure increased from an average of about 80 psi to about 180 psi with the increase in flow rate. As shown in FIG. 21, the liquid flow rate of 10 μL/sec, the % buprenorphine HCl recovery on the filter was about 86%, and the total recovery was about 100%. As shown in FIG. 22, for the liquid flow rate of 20 μL/sec, the % buprenorphine HCl recovery on the filter was increased to about 91%, and the total recovery approached 100%.

In a further test, the CAG heater included a flow passage of K32EG tubing having a length of 35 mm and a formed tip constriction with an open cross-sectional area of 3257 μm$^2$. A liquid formulation containing 1.5% buprenorphine HCl in 95% ethanol/5% water was supplied to the flow passage at flow rates of 10 μL/sec and 20 μL/sec. The observed operating pressure increased from an average of about 130 psi to about 250 psi with the increase in flow rate. As shown in FIG. 23, for the liquid flow rate of 10 μL/sec, the % buprenorphine HCl recovery on the filter was up to about 87%, and the total recovery was about 100%. As shown in FIG. 24, for the liquid flow rate of 20 μL/sec, the % buprenorphine HCl recovery on the filter was increased to about 91%, and the total recovery was about 100%.

EXAMPLE 6

Tests were conducted to evaluate aerosol production using a CAG heater with a liquid formulation containing 100% water as the carrier and 3% cromolyn sodium. The liquid flow rate was 20 μL/sec. The CAG heater included a flow passage of K32EG tubing having a length of 35 mm. Untipped CAG heater constructions including an unconstricted capillary passage (i.e., having the same internal diameter along the length thereof), and tipped capillary passages having a formed tip constriction with respective open cross-sectional areas of 903 μm$^2$ and 3280 μm$^2$ were tested. As shown in FIG. 25, the % cromolyn sodium recovery was about 10% for the capillary passage without a constriction. The % cromolyn sodium recovery was significantly increased by using a CAG with a constriction at the outlet thereof. The highest aerosol recovery was measured for the constriction with the smaller open cross-sectional area. The test results demonstrate that high aerosol recoveries can be achieved using a carrier of 100% water, over a broad range of applied power levels.

In another comparative test, an aerosol was produced using a CAG heater including an unconstricted flow passage of 35 gauge tubing with the same liquid formulation supplied at a flow rate of 20 μL/sec. The average mass median aerodynamic diameter (MMAD) of the cromolyn sodium aerosol particles was about 1.6 μm. In a comparative test, an aerosol was produced using a CAG heater including a constricted flow passage of 35 gauge tubing having a formed tip constriction with an inner diameter of about 0.002 inch, with the same liquid formulation supplied at the same flow rate. The average MMAD of the cromolyn sodium aerosol particles was about 0.8 μm, demonstrating that the particle size decreases as the size of the constriction decreases. It is hypothesized that this result is due to a higher vapor velocity inside of the smaller tip inner diameter of the capillary, producing a larger shear of droplets entrained inside the tip, causing the formation of smaller particles.

In a further comparative test, the effect on cromolyn sodium aerosol particle size of adding a low-volatility substance to a liquid formulation was evaluated. The liquid formulation contained 100% water as the carrier, 3% cromolyn sodium and respective concentrations of 0%, 5% and 10% glycerol, a low-volatility compound. The liquid flow rate was 10 μL/sec. Aerosol was produced using a tipped CAG heater including a flow passage of 35 gauge tubing with a constricted tip. The cromolyn sodium aerosol particle MMAD sizes were determined to be 1.6 µm, 2.2 µm and 3.0 µm for the 0%, 5% and 10% glycerol concentrations, respectively.

EXAMPLE 7

Tests were conducted to demonstrate that insulin aerosols of a desirable aerosol particle size can be produced using embodiments of the tipped CAG that include a constricted capillary passage. The tipped CAG included a flow passage having a length of 35 mm and a formed tip constriction having a length of about 0.02 inch and an open diameter of about 0.002 inch. Two different liquid insulin formulations were tested, the first formulation containing HUMULIN R, which is available from Eli Lilly and Company, located in Indianapolis, Ind. The HUMULIN R formulation had an insulin concentration of 500 units/ml. The other insulin formulation was an extemporaneous formulation of 2% human insulin (SIGMA, product no. 10259, which is available from Sigma-Aldrich, Inc., located in Saint Louis, Mo.) in an aqueous solution of 90% water/10% 0.1 N HCl. The flow rate of both liquid formulations was 10 µL/sec. It should be appreciated that each of these formulations can be considered to be a highly volatile liquid for the purposes of producing aerosols with a tipped CAG.

TABLE 1 shows the test results for aerosol production using the HUMULIN R formulation for different applied power levels. The insulin aerosol particle MMAD and the % fine particle fraction, i.e., the percentage of the total number of insulin particles analyzed that had a particle size of less than about 5 µm, are shown. The aerosol particle size was determined using a multiple-stage MOUDI cascade impactor, which is available from MSP Corporation, located in Shoreview, Minn. The cascade impactor was arranged downstream of an L-shaped tube (elbow) in fluid communication with the outlet end of the flow passage. The insulin aerosol particles had a maximum MMAD of 2.0 µm and a minimum % fine particle fraction of about 81%. FIGS. 26 and 27 are scanning electron microscope micrographs at a magnification of 7,000× and 15,000×, respectively, showing aerosolized insulin particles that were produced.

TABLE 1

| Test No. | Insulin Formulation | Applied Power (watts) | MMAD (µm) | % Fine Particle Fraction |
|---|---|---|---|---|
| 1 | HUMULIN R | 10.0 | 1.4 | 86.21 |
| 2 | HUMULIN R | 9.8 | 1.5 | 81.35 |
| 3 | HUMULIN R | 10.1 | 1.5 | 85.96 |
| 4 | HUMULIN R | 9.7 | 2.0 | 87.22 |
| 5 | HUMULIN R | 9.6 | 1.8 | 86.75 |

TABLE 2 shows the test results for aerosol production using the extemporaneous insulin formulation. The insulin aerosol particles had a maximum MMAD of 2.1 µm for three levels of power (11.4, 11.8 and 12.4 watts) applied to the heater. The % fine particle fraction of the aerosol particles was over 50% for all of the applied power levels.

TABLE 2

| Test No | Insulin Formulation | Applied Power (watts) | MMAD (µm) | % Fine Particle Fraction |
|---|---|---|---|---|
| 6 | Extemporaneous Formulation | 11.4 | 1.4 | 80.6 |
| 7 | Extemporaneous Formulation | 11.8 | 1.1 | 85.9 |
| 8 | Extemporaneous Formulation | 12.4 | 1.3 | 82.1 |
| 9 | Extemporaneous Formulation | 8.7 | 2.1 | 53 |

As explained in commonly-assigned U.S. patent application Ser. No. 10/648,282, the electrode at the downstream or exit end of the heated section of an untipped CAG is provided with a predetermined electrical resistance which causes the electrode to heat up when voltage is applied, and thereby minimize a temperature gradient between the wall of the capillary tube at the downstream end of the heated section and the downstream electrode. The electrical resistivity, cross-sectional area, and length of the electrode at the downstream end of the heated section can be selected to minimize or eliminate such temperature gradient and prevent the downstream electrode from acting as a heat sink, thereby minimizing loss of heat from the downstream end of the heated section. The electrical resistivity of the downstream electrode that achieves the optimum balancing of heat transfer along the capillary tube may be selected to accommodate changes in the thermal profile as a function of the desired flow rate of fluid and/or vapor through the tube. Surprisingly, the tipped CAG can produce aerosols having desirable emitted and respirable fractions without the need for a specially designed downstream electrode.

EXAMPLE 8

Tests were conducted to evaluate aerosol production using a CAG heater without a high resistance downstream electrode. The tests were carried out using a Cu—Be gold-plated downstream electrode attached directly to a flow passage of K32EG tubing having a length of 25 mm and a formed tip constriction with an open cross-sectional area of 2582 µm². A liquid formulation containing 1.5% buprenorphine HCl in 95% ethanol/5% water was supplied to the flow passage at a flow rate of 10 µL/sec. As shown in FIG. 28, the % buprenorphine HCl recovery on the filter ranged from about 80% to about 94%, and the total recovery was about 100%, over a broad applied power range of about 5 watts to about 9.7 watts. In a second test, the capillary passage length was 35 mm. As shown in FIG. 29, the % buprenorphine HCl recovery on the filter ranged from about 85% to about 94%, and the total recovery was about 100%, over an applied power range of about 7 watts to about 9 watts.

By attaching an electrode of a good electrical conductor, such as Cu—Be, directly to the flow passage of a material, such as stainless steel having a higher resistance than the electrode, manufacturing of tipped CAG heaters can be simplified and/or production costs can be lowered.

EXAMPLE 9

It has been determined that the tipped CAG can provide desired aerosol production for various medicament containing formulations over a wide range of heater power levels. Tests were conducted to evaluate aerosol recoveries at reduced applied power levels. The CAG heater included a flow passage of K32EG tubing having a length of 25 mm and a formed tip constriction with an open cross-sectional area of 2400 µm². The CAG heater did not include a high resistance downstream electrode. A liquid formulation containing 1.5% buprenorphine HCl in 95% ethanol/5% water was supplied to the flow passage at a flow rate of 20 µL/sec The minimum amount of delivered power required for complete vaporization of this formulation can be calculated to be about 16 watts. As shown in FIG. 30, however, the % buprenorphine HCl recovery on the filter ranged from about 70% to about 90%, and the total recovery was about 100%, over a broad applied power range of about 6 watts to 17 watts. Accordingly, the test results demonstrate that CAG heaters including a constricted flow passage provided desirable aerosol recoveries at power levels as low as about 35% of the value calculated for 100% vaporization to occur.

By providing the capability of producing desirable aerosol recoveries at lower than expected power levels, the CAG heaters including a constricted flow passage also provide the capability of producing increased doses of liquid formulations, such as a larger dose of medicaments, e.g., 40 µL doses versus 20 µL doses with an unconstricted flow passage. For example, due to the ability to generate desired aerosol recoveries at lower power levels, higher flow rates of the liquid formulations can be vaporized in a preset delivery time. In addition, the CAG heaters provide the capability of producing a given dose of a liquid formulation, for example, a 20 µL dose of a medicament using a smaller power supply, for example, smaller sized and weight batteries.

The test results described in Examples 8 and 9 and illustrated in FIGS. 28-30 demonstrate unexpected advantages of the tipped CAG. Very high filter recoveries were obtained in each of those examples over a wide range of applied power. These include a power range of 5 to approximately 9.75 amps as illustrated in FIG. 28 and a range of 6 to 17 amps as illustrated in FIG. 30. A smaller but still significantly expanded power range is illustrated in FIG. 29.

An unexpected advantage of the tipped CAG is that the amount of power necessary to vaporize the liquid in the CAG was less than would have been predicted on a theoretical basis. For example, in FIG. 28, the theoretical calculated amount of power necessary to vaporize the particular liquid formulation was approximately 8 watts. Surprisingly high recoveries were observed with an applied power of as low as 5 watts, a power level over 30% below the calculated power level to obtain 100% vaporization. Similar results were obtained for the experiments conducted and illustrated in FIGS. 29 and 30. It follows that when the tipped CAG is incorporated in a handheld aerosol generator, operational power requirements and thus battery capacity may potentially be reduced. A reduced but still acceptable battery capacity could lead to a more compact handheld inhaler design. Another advantage is that the control system used in an aerosol generator incorporating a tipped CAG can be simplified since it need not have the capability to maintain the power delivered to the heater within an extremely narrow range. It follows that the associated control circuitry and processes may be less complex and potentially less expensive to design and manufacture inhalers incorporating a tipped CAG.

FIG. 25 shows that relatively low filter yields were obtained using an unconstricted CAG over a very wide power range. Tipped CAGs, on the other hand, were able to provide substantially higher filter yields ranging from about 40% to about 80% over not only a wide power range but also a power range as low as approximately 5 watts which is well below the 16 watt calculated amount of power to fully vaporize the liquid formulation. It will be readily appreciated that the tipped CAG offers considerable flexibility in the design and manufacture of inhalers used to deliver liquid formulations in aerosol form.

While the invention has been illustrated and described in accordance with preferred embodiments, it is recognized that variations and changes may be made therein without departing from the invention as set forth in the claims.

What is claimed is:

1. An aerosol generator, comprising:
   a flow passage including an inlet end, an expelling end and a first flow section;
   a constriction at the expelling end of the flow passage, the constriction defining a second flow section of the flow passage downstream from the first flow section; and
   a heater arranged along the flow passage which heats liquid in the first flow section to produce vapor and liquid which is expelled from the outlet expelling end into ambient air;
   wherein the constriction is adapted to create sufficiently high fluid shear forces to break up droplets of the liquid into smaller droplets.

2. The aerosol generator of claim 1, wherein the first flow section of the flow passage has a first transverse cross-sectional area which is larger than a second transverse cross-sectional area of the second flow section of the flow passage at the expelling end, and the ratio of the first transverse cross-sectional area to the second transverse cross-sectional area is about 2:1 to up to about 30:1.

3. The aerosol generator of claim 1, wherein the flow passage and the constriction are of the same material or of a different material, the material being selected from group consisting of metals, ceramics, glasses, plastics, polymers, and combinations thereof.

4. The aerosol generator of claim 1, wherein the second flow section has a round or a non-round transverse cross-section.

5. The aerosol generator of claim 1, wherein the flow passage and the constriction are of a metallic material.

6. The aerosol generator of claim 1, wherein the first flow section and the second flow section of the flow passage are capillary-sized.

7. The aerosol generator of claim 1, wherein the flow passage has a maximum transverse dimension of from about 0.025 mm to about 0.25 mm.

8. The aerosol generator of claim 1, wherein the flow passage comprises a metallic tube and the constriction is a crimped end of the metallic tube.

9. The aerosol generator of claim 8, wherein the second flow section at the crimped end has a circular or non-circular transverse cross section.

10. The aerosol generator of claim 8, wherein the second flow section has a cross-sectional area of about 500 µm² about 51,000 µm².

11. The aerosol generator of claim 8, wherein the crimped end has a length of about 0.5 mm to about 3 mm.

12. The aerosol generator of claim 1, wherein the flow passage comprises multiple pieces including opposed surfaces that are joined together along an interface to define the first and second flow sections therebetween.

13. The aerosol generator of claim 12, wherein the two portions of the flow passage are molded, cast or machined.

14. The aerosol generator of claim 1, wherein the flow passage is capillary-sized and comprises a capillary tube, a monolithic body, or a laminated structure.

15. The aerosol generator of claim 1, wherein the flow passage includes a third flow section near the expelling end of the flow passage, wherein the vapor and liquid is cooled as it is expelled.

16. The aerosol generator of claim 15, wherein the third flow section includes a cooling device in contact with the flow passage and wherein the temperature of the third flow section is reduced by about 10° C. to about 100° C.

17. The aerosol generator of claim 16, wherein the temperature of the third flow section is reduced by about 50° C. to about 70° C.

18. The aerosol generator of claim 16, wherein the cooling device is a heat sink.

19. The aerosol generator of claim 18, wherein the third flow section is within the first flow section and adjacent to the second flow section.

20. The aerosol generator of claim 1, wherein the constriction has a length of about 3 mm to about 6 mm.

21. The aerosol generator of claim 1, wherein the flow passage is a capillary-sized tube and the constriction is a partial closure of the capillary-sized tube at the expelling end.

22. A handheld aerosol generator, comprising:
a flow passage including an inlet end, an expelling end and a first flow section;
a constriction at the expelling end of the flow passage, the constriction defining a second flow section of the flow passage downstream from the first flow section;
a heater arranged along the flow passage which heats liquid in the first flow section to produce a vapor and liquid which is expelled from the expelling end; and
a mouthpiece in fluid communication with the expelling end of the flow passage through which a user can draw aerosol from the aerosol generator;
wherein the constriction is adapted to create sufficiently high fluid shear forces to break up droplets of the liquid into smaller droplets.

23. The aerosol generator of claim 22, wherein the flow passage includes a third flow section near the expelling end of the flow passage, wherein the vapor is cooled as it is expelled, and wherein the third flow section includes a cooling device in contact with the flow passage and wherein the temperature of the third flow section is reduced by about 10° C. to about 100° C.

24. The aerosol generator of claim 23, wherein the temperature of the third flow section is reduced by about 50° C. to about 70° C.

25. The aerosol generator of claim 23, wherein the cooling device is a heat sink.

26. An aerosol generator, comprising:
a flow passage including an inlet end, an expelling end and a first flow section;
a constriction at the expelling end of the flow passage, the constriction defining a second flow section of the flow passage downstream from the first flow section;
a liquid source in flow communication with the inlet end of the flow passage, the liquid source containing a liquid formulation including a medicament; and
a heater arranged along the flow passage which heats the liquid formulation in the first flow section to produce a vapor and liquid which is expelled from the expelling end so as to form an aerosol;
wherein the constriction is adapted to create sufficiently high fluid shear forces to break up droplets of the liquid into smaller droplets.

27. The aerosol generator of claim 26, wherein the liquid source contains a liquid comprising at least one medicament selected from the group consisting of insulin, buprenorphine hydrochloride, cromolyn sodium, albuterol sulfate, isoproterenol sulfate, metaproterenol sulfate, terbutaline sulfate, pirbuterol acetate, salmeterol xinotoate, formotorol, beclomethasone dipropionate, flunisolide, fluticasone, budesonide, triamcinolone acetonide, beclomethasone dipropionate, triamcinolone acetonide, flunisolide and fluticasone.

28. The aerosol generator of claim 26, wherein the liquid source contains a medicament selected from the group consisting of analgesics, anginal preparations, anti-allergics, antibiotics, antihistamines, antitussives, bronchodilators, diuretics, anticholinergics, hormones and anti-flammatory agents.

29. The aerosol generator of claim 26, wherein the liquid source contains a single dose or multiple doses of the medicament.

30. The aerosol generator of claim 26, wherein the liquid formulation comprises a medicament, a highly-volatile carrier and optionally a low-volatility carrier.

31. The aerosol generator of claim 30, wherein the highly-volatile carrier comprises (i) about 20-80 volume % water and about 80-20 volume % ethanol or (ii) about 80-100 volume % water and up to about 20 volume % ethanol.

32. The aerosol generator of claim 26, further comprising:
a power supply;
a valve disposed between the liquid source and the flow passage; and
a controller operable to actuate the valve to control flow of the liquid from the liquid source to the inlet end of the flow passage and to control the delivery of power from the power supply to the heater to maintain the heater at a temperature range effective to vaporize liquid in the flow passage.

33. The aerosol generator of claim 26, wherein the liquid source is removably attachable to the aerosol generator.

34. The aerosol generator of claim 26, wherein the flow passage includes a third flow section near the expelling end of the flow passage, wherein the vapor and liquid is cooled as it is expelled, and wherein the third flow section includes a cooling device in contact with the flow passage and wherein the temperature of the flow passage expelling end is reduced by about 10° C. to about 100° C.

35. The aerosol generator of claim 34, wherein the temperature of the third flow section is reduced by about 50° C. to about 70° C.

36. The aerosol generator of claim 34, wherein the cooling device is a heat sink.

37. The aerosol generator of claim 34, wherein the third flow section is within the first flow section and adjacent to the second flow section.

38. An aerosol generator, comprising:
a flow passage including an inlet end, an expelling end and a first flow section;
a constriction at the expelling end of the flow passage, the constriction defining a second flow section of the flow passage downstream from the first flow section;
a heater arranged along the flow passage;
a power supply adapted to supply power to the heater; and
a controller controlling operation of the power supply to supply an effective amount of power to the heater to heat liquid in the first flow section to produce a vapor and liquid which is expelled from the expelling end;
wherein the constriction is adapted to create sufficiently high fluid shear forces to break up droplets of the liquid into smaller droplets.

39. The aerosol generator of claim 38, wherein the flow passage includes a third flow section near the expelling end of the flow passage, wherein the vapor and liquid is cooled as it is expelled, and wherein the third flow section includes a cooling device in contact with the flow passage and wherein the temperature of the flow passage expelling end is reduced by about 10° C. to about 100° C.

40. An aerosol generator, comprising:
a flow passage including an inlet end, an expelling end and a first flow section;
a constriction at the expelling end of the flow passage, the constriction defining a second flow section of the flow passage downstream from the first flow section; and
a heater arranged along the flow passage which heats liquid in the first flow section to produce vapor and liquid which is expelled from the expelling end so as to form an aerosol, a first electrode attached to the heater and a second electrode attached to the heater downstream of the first electrode, the second electrode being of a material that has a smaller resistance than a material of the heater;
wherein the constriction is adapted to create sufficiently high fluid shear forces to break up droplets of the liquid into smaller droplets.

41. The aerosol generator of claim 40, wherein the flow passage is of stainless steel and the second electrode is of a Cu—Be alloy.

42. A method of producing an aerosol, comprising:
supplying a liquid to the inlet end of a flow passage including an expelling end, a first flow section and a constriction at the expelling end, the constriction defining a second flow section of the flow passage downstream from the first flow section; and
heating the liquid in the first flow section to produce vapor and liquid which is expelled from the expelling end into ambient air;
wherein the constriction is adapted to create sufficiently high fluid shear forces to break up droplets of the liquid into smaller droplets.

43. The method of claim 42, wherein only a portion of the liquid in the first flow section is vaporized by heating.

44. The method of claim 42, wherein the heating includes applying a power level that is less than a theoretical power level for vaporizing 100 % of the liquid to a heater to heat the liquid in the first flow section.

45. The method of claim 42, wherein the liquid comprises at least one medicament selected from the group consisting of insulin, buprenorphine hydrochloride, cromolyn sodium, albuterol sulfate, isoproterenol sulfate, metaproterenol sulfate, terbutaline sulfate, pirbuterol acetate, salmeterol xinotoate, formotorol, beclomethasone dipropionate, flunisolide, fluticasone, budesonide, triamcinolone acetonide, beclomethasone dipropionate, triamcinolone acetonide, flunisolide and fluticasone.

46. The method of claim 42, wherein the liquid contains a medicament selected from the group consisting of analgesics, anginal preparations, anti-allergics, antibiotics, antihistamines, antitussives, bronchodilators, diuretics, anticholinergics, hormones and anti-flammatory agents.

47. The method of claim 46, wherein the liquid comprises a medicament and a highly-volatile carrier.

48. The method of claim 47, wherein the highly-volatile carrier is selected from the group consisting of water, ethanol and mixtures thereof.

49. The method of claim 42, wherein the liquid comprises a high-volatility carrier and insulin.

50. The method of claim 42, including producing the aerosol with a handheld inhaler.

51. The method of claim 42, including:
supplying power to the heater with a power supply; and
controlling operation of the power supply with a controller to supply an effective amount of power to the heater to heat the liquid formulation in the first flow section to produce a vapor and liquid which is expelled from the expelling end.

52. The method of claim 42, further comprising cooling the vapor in a third flow section as it is expelled, wherein the third flow section is in a downstream portion of the first flow section and includes a cooling device in contact with the flow passage, and wherein the temperature of the temperature of the third flow section is reduced by about 10° C. to about 100° C.

\* \* \* \* \*